(12) United States Patent  
Spranza et al.

(10) Patent No.: US 7,938,810 B2
(45) Date of Patent: May 10, 2011

(54) SAFE TROCHAR WITH GUIDE FOR PLACEMENT OF SURGICAL DRAINS

(76) Inventors: Joseph J. Spranza, Grass Valley, CA (US); Robert S. Namba, Corona del Mar, CA (US)

( * ) Notice: Subject to any disclaimer, the term of this patent is extended or adjusted under 35 U.S.C. 154(b) by 1724 days.

(21) Appl. No.: 10/697,444

(22) Filed: Oct. 29, 2003

(65) Prior Publication Data

US 2004/0092891 A1    May 13, 2004

Related U.S. Application Data

(63) Continuation-in-part of application No. 09/697,463, filed on Oct. 26, 2000, now Pat. No. 6,613,039.

(51) Int. Cl.
*A61M 5/00* (2006.01)
*A61F 11/00* (2006.01)

(52) U.S. Cl. ........................................ 604/264; 606/108

(58) Field of Classification Search .......... 604/540–544, 604/164.01, 264, 263, 158, 164.1, 167.01, 604/192, 110, 111; 606/108, 222; 128/919
See application file for complete search history.

(56) References Cited

U.S. PATENT DOCUMENTS

| 2,581,564 | A | * | 1/1952 | Villegas | 606/225 |
| 4,345,601 | A | * | 8/1982 | Fukuda | 606/147 |
| 5,669,882 | A | * | 9/1997 | Pyles | 604/170.03 |
| 5,779,680 | A | * | 7/1998 | Yoon | 604/164.12 |
| 6,004,294 | A | * | 12/1999 | Brimhall et al. | 604/164.08 |

* cited by examiner

*Primary Examiner* — Nicholas D Lucchesi
*Assistant Examiner* — Nathan R Price
(74) *Attorney, Agent, or Firm* — Black Lowe & Graham PLLC

(57) ABSTRACT

A method and apparatus for the safe surgical placement of trochars, is provided. The trochar has a sheath protecting the sharp point. The guide includes a receiver, into which the trochar with sheath is inserted, protecting personnel against sticks. The guide has a holder that grips the trochar in the X, Y, Z and Theta directions, providing position and direction of the point. The guide provides a handle for holding the trochar, reducing effort. The trochar point is exposed only after opening the guide. The receiver with sheath is a target, which provides an accurate reference for the position of the sharp point. The target also provides support as the trochar is being advanced through soft tissue. The trochar is locked into the safety guide until the guide is closed, and the point is safely in the sheath. Since the guide may not be reopened, the trochar point and body fluids are safely covered. Operating Room personnel are protected against hazardous sharps injuries.

12 Claims, 21 Drawing Sheets

SAFE TROCHAR WITH GUIDE FOR PLACEMENT OF SURGICAL DRAINS

This is a Continuation in Part application for Safety Guide for Surgical Placement of Sharp Instruments, Originally filed Oct. 26, 2000 Ser. No. 09/697-463, issued as Pat. No. 6,613,039 Divisional Application Filed 3 Jul., 03, Ser. No. 10/613,387

BACKGROUND

1. Field of Invention

In the field of surgery, this invention relates to a safety device for handling and advancing a safe trochar through a patient's soft tissue, including the dermal layers.

2. Description of Prior Art

The implementation of safety measures in the workplace of health-care personnel, such as physicians, nurses and phlebotomists, has lagged behind such implementation in other industries. Nurses have been concerned with hazards posed by sharp devices associated with their practices and have joined other medical practitioner groups to push for safer hardware, workplace environments, and injury reporting. As an answer to the problem, in the 1990s several states enacted laws concerning health-care worker safety. In 2000, the President of the United States signed into effect the "Needlestick Safety and Prevention Act" (H. R. 5178) requiring health-care facilities to use "Safe Medical Devices". A limited number of devices are now available that diminish the exposure of health-care personnel to scratches and puncture wounds and contamination by potentially dangerous body fluids or chemicals which may lead to infection. Such pathogens as HIV, Hepatitis B, Hepatitis C, staphylococcus and streptococcus bacteria and others, may be transferred from the patient to health-care workers by scratches and puncture wounds. The American Nurses Association (ANA) reports that more than twenty diseases can be transmitted through sharps or needlestick injuries. The newly available devices include convenient safety sheaths around hypodermic needles and intravenous medication bottles. The nature of surgical procedures, however, unavoidably exposes medical personnel, including surgeons, assistants, and nurses, to many other sharp and potentially injurious instruments. The instruments include not only needles, but also trochars, scalpels, retractors and many other sharp and pointed tools. The National Institute for Occupational Safety and Health (NIOSH) reports that "while the exact number of needlestick injuries is not available, it is estimated there are 600,000 to 1,000,000 needlestick injuries in the United States per year, resulting in up to 1,000 new cases of HIV, Hepatitis B or Hepatitis C annually."

One of the most dangerous of sharp instruments used in surgery is the trochar; an elongated, highly polished spear-like instrument, utilized, amongst other purposes, to make stab wounds in soft tissue for the placement of surgical drains. Until the hardware of the present invention, no safe trochar has been available.

Surgical drains are used in a wide variety of surgical procedures. The drains are tubular and made of soft materials; plastics and rubbers being common. One end of such a drain is placed in a body cavity and the other end extends outside of the patient's body. The drain exits the body through a stab wound, created by a trochar, in the soft tissue through the skin. The drain carries fluids into a reservoir attached to the other end of the drain tube. The drain facilitates the removal of an unwanted collection of fluid, including serum, blood, bile and/or waste materials such as pus. In addition to conducting waste materials, drains may serve as salvage devices. In a procedure known as "autologous transfusion", using drains after deep tissue surgery, blood may be collected, washed or unwashed, and transfused into the patient's body.

It will be appreciated from the above, that many surgical drains are installed daily. Since most surgical drains are inserted through the skin with trochars, it is obvious that a safe trochar is a much-needed device. Before the hardware of this invention, no trochar was available which provided built-in safety features for installing surgical drains. In this invention, a safe trochar is provided. The hardware of this invention also provides a safety guide for enhancing the handling of this safety trochar and for protecting OR personnel.

Trochars often have plastic protective sheaths when presented to the sterile field in the Operating Room. Such a protective sheath covers the trochar's sharp point and reduces damage during shipping and handling. The removal of the plastic protective sheath, necessary prior to use of the trochar, is a bit tedious. Often times, the plastic sticks to the trochar and resists removal. When it does finally slide off, the resulting sudden reaction causes the protective sheath to go in one direction and the trochar in another. The sharp point may contact something or someone in the process. The sharp point may be damaged, or someone may be cut or stabbed. The hardware of this invention provides a protective sheath that is installed before shipping. This protective sheath is on the safety trochar as presented into the sterile field. But, OR personnel do not have to remove this protective sheath; the trochar automatically slides out of the sheath by action of the safety guide.

The sharp points of trochars are available in several different designs. One design has three flat surfaces (facets) evenly spaced around the diameter of the rod and angled so that the surfaces come to a point at end of the rod, on the rod's linear axis. Another design has only two flat surfaces leaving intact a portion of the original radius of the rod. In both three facet and two facet point designs, the flat surfaces intersect to form a ridge. This ridge is sharp enough to cut tissue when enough pressure is exerted. In fact, the cutting of the tissue by the ridge between the facets reduces the force required to drive the trochar through soft tissue. Another design of the sharp point of trochars is a simple cone. The force required to push a cone point trochar through soft tissue is somewhat greater than that required to push a faceted sharp point through soft tissue. However, there are advantages to a cone point trochar. A hole pierced with a cone point appears to show less evidence of trauma to the surrounding tissue than one pierced with a faceted point. Yet a different point design has a compound cone: two or more cone angles are utilized, sequentially, along the point. There are about a dozen sharp point designs in trochars. The safety hardware of this invention is designed to work with, if not all, at least a majority of the designs.

Formerly, trochars were handled manually. Until the hardware of this invention, there was no safety device available to protect surgical personnel from sticks and scratches from trochars used for placing drains and for similar through-the-tissue passage. The sharp instrument was grasped, directed and advanced by hand. The surgeon wears gloves. The trochar is a highly polished, hard thin rod. The environment is slippery. Often, visibility is obscured. Pushing a trochar through tissue can require some force. Any force, rotational or linear must be obtained through friction between wet, bloody gloves and wet slippery metal. So, the grip by the surgeon's hand onto the trochar must be significantly high. The higher grip required was fatiguing. Fatigue leads to errors. The hardware of this invention serves as a handle for the trochar. The handle holds the trochar firmly and the handle is shaped to fit the surgeon's hand without slipping. No slipping means less gripping force required and therefore, less fatigue.

Most trochars have a curve at the mid-length of the rod. The pointed end (herein called the first end) is at an angle to the butt (opposite) end (herein called the second end). The first end is built upon a right circular cylinder, as is the second end. Joining these two straight rod ends is a curve. The result is an instrument that looks somewhat like a sailmaker's needle. The curve in the trochar allows a more normal (right angle) angle of contact between the sharp pointed "piercing end" of the instrument and the tissue, because the angle allows the second end to clear obstructions in close spaces. Formerly, as described above, installing a surgical drain, or performing other procedures requiring a rod-like sharp instrument, required holding the instrument by hand and exposing surgical personnel to the sharp pointed end of that instrument; before, during and after the instrument had been through the tissue of the patient. Former trochars had no "indicators" on the second end to tell the surgeon where the pointed end (which is hidden) was directed. It was patently hazardous to have the point emerge in an unexpected place. The hardware of this invention provides a safety guide that by design holds the safety trochar in such a manner so that the surgeon knows exactly where the trochar is pointing.

A trochar for drain placement typically enters the patient's soft tissue from inside the body cavity and exits to the outside through the overlying skin. Great care must be taken in avoiding injury to vital structures while the trochar is being inserted. Great care must also be taken to avoid driving the sharp end into oneself or an assistant as it exits the soft tissue. There is a layer of adipose tissue inside the body, beneath the dermal layers. This fat layer may be as thin as 10 mm but often is much thicker; it is not uncommon to encounter 75 mm or even thicker. Since the trochar is curved, and since it is being held on the second end, the sharp point tends to deflect away from the tissue when any resistance is encountered. The instrument revolves within the surgeon's slippery gloved hand, the point on the curved end aiming in a new direction. Unfortunately, before now, there has been no target mechanism to tell the surgeon where the sharp point of the trochar will emerge from the tissue. So, the sharp point may poke through where it is not expected, where it is not wanted. If the hand backing up the tissue is where the point emerges, then, the surgeon or assistant is impaled. On its way through the patient's tissue, the trochar becomes coated with body fluids from the patient and this must be considered hazardous. The hardware of this invention provides a target so that the surgeon knows exactly there the point will emerge from the soft tissue.

It is necessary to hold tissue through which a sharp instrument is being driven. Holding the tissue prevents slipping. Holding also reduces stretching the tissue. But, with previous sharp angled instruments it was difficult to know where the sharp point would emerge. A good method of "backing up" the tissue right in the path of the trochar, was needed. The hardware of this invention provides a target which not only indicates exactly where the sharp point is aimed, this target also provides a support, a back up system to hold the tissue as the sharp point is being advanced through it.

When the sharp point emerges after passing through the tissue, the trochar must be pulled all the way through the tissue, followed by some of the drain tube. The trochar is hard, highly polished and is made even more slippery by body fluids picked up in passing through the patient's tissue. Of course, grasping the pointed end with gloved fingers is not a very good method of pulling the trochar, at least not initially. How does one grasp a slippery cone at the pointed end?

Therefore, the surgeon or assistant needed to pick up a grabber like a forceps or pair of pliers. However, the pliers and forceps are also hard and well polished. The result is that the task of grabbing and pulling a sharp-pointed, hazardously coated, slippery rod requires some force and a lot of care. With the hardware of this invention, the sharp point of the safe trochar automatically enters the target assembly. Further, the safe trochar of this invention is automatically guided into the safety sheath, upon protruding from the soft tissue, and it is locked therein. The safety guide provides an ergonomically correct handle for effortlessly pulling the captured trochar the rest of the way through the tissue.

Formerly, after pulling the used trochar through the soft tissue, a surgeon had to hold the trochar in his gloved hand and cut it free from the drain tube. The sharp point of the trochar was exposed and it was wet and hazardous. With the hardware of this invention, the trochar sharp point is safely locked into the sheath, completely harmless.

A further feature of this hardware is that the trochar may not be used a second time. The safety guide will not re-open and expose the sharp point of a used trochar. When the guide is closed, there is no way to release the trochar a second time from the safety sheath.

OBJECTS AND ADVANTAGES

Accordingly, several objects and advantages of our hardware are:

The hardware of this invention is the first hardware invented to provide integrated safety features for installing trochars that pass completely through soft tissue to advance a drain tube.

This safe trochar of this invention is shipped and presented with a hard safety sheath that does not require removal by Operating Room personnel.

The safety sheath on this hardware will work over a number of different point designs: conical point, compound conical point, two, three or four facet point, or a combination of point designs.

The safety guide holds the trochar in all dimensions (directions X, Y, Z, and theta) for user safety and convenience. Further, the guide will not release the trochar until the point is safely locked into the safety sheath.

This safety guide provides a good grip for the surgeon—it has a handle which provides grip even in a slippery environment.

The position and direction of the pointed end on this safe trochar is known at all times, and coincides with the target. The integral target indicates exactly where the point will emerge from soft tissue.

Soft tissue is backed up and supported by the target, an integral part of the guide.

After passing through soft tissue, the sharp point of this safe trochar enters the target and becomes locked therein.

The safety guide becomes a handle for pulling the trochar through the soft tissue. A hinge mechanism provides for a natural wrist action to convert from piercing to pulling.

When the trochar enters the target after one tissue piercing, it is locked therein, and may not be removed from the safety sheath a second time.

A safety key ensures that the safe sheath may not be removed from the trochar if the trochar is not in the safety guide.

Further to the above feature, the trochar is locked into the guide until the guide is closed and the trochar point is safely entered into the sheath.

And, the safe trochar may not be used a second time.

Further objects and advantages are to provide hardware that requires neither additional skill nor work to perform a formerly hazardous task—safely, easily and quickly. It is another object and advantage to provide hardware that reduces the number of other devices and discrete steps required to perform a procedure. Still further objects and advantages will become apparent from a consideration of the ensuing description and drawings.

DRAWING FIGURES

In the drawings, closely related figures have the same number but different alphabetic suffices.

Figure 1:
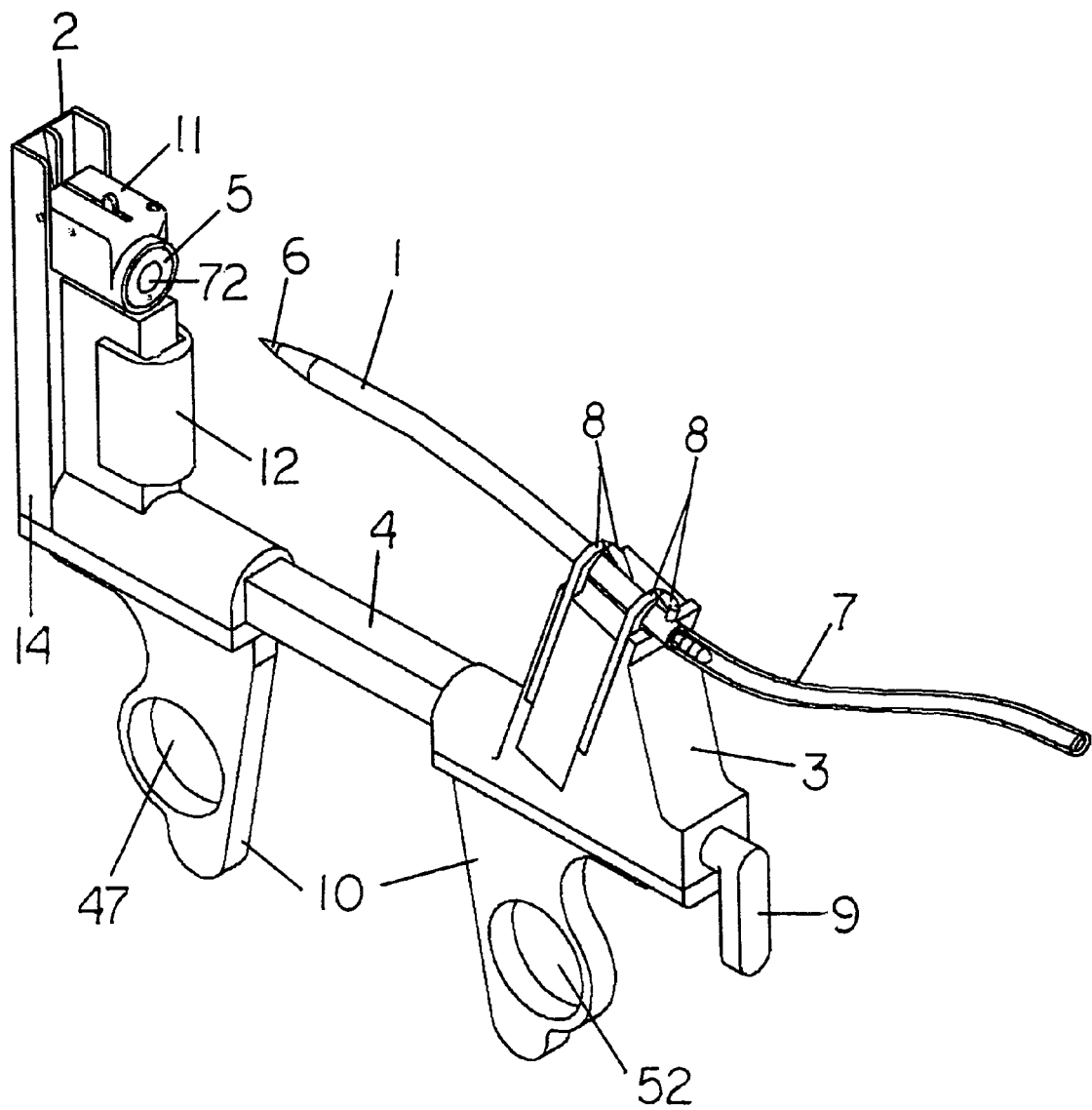
FIG. 1 shows an isometric view of the safety guide and safe trochar.

REFERENCE NUMERALS IN DRAWINGS 1. trochar (sharp instrument)
2. receiver mechanism
3. holder mechanism
4. support and alignment beam
5. target end plate
6. sharp point
7. drain tube
8. holder element levers
9. reset lever
10. (*a*) and (*b*) handles
11. receiver
12. thumb press bar
13. safety sheath
14. receiver standard
15. pivot for receiver
16. ridge for release
17. sheath retaining pawl
18. carriage for receiver standard
19. carriage for holder standard
20. V groove in holder
21. ward
22. locking vane
23. spring for lock vane
24. guide body for sharp end of sharp instrument
25. housing for safety sheath and 25(*a*), first end plate
26. conical cavity for sharp point
27. locked vane
28. receiver "down" indicator button
29. key
30. and/or beam
31. crickle
32. boot
33. feet, *a* and *b*
34. slot for boot "down"
35. spring, holder actuator
36. (*a*) and (*b*) levers, force multiplying
37. block, actuator
38. torsion rod
39. pivot pin, element
40. jack, (push up A)
41. pushrod, boot
42. jack, (push up B)
43. 1-2 vane
44. pawl, 1-2 lock
45. spring, pawl
46. lock groove, 1-2 lock
47. finger hole
48. pivot, pawl
49. tail, pawl
50. nose, pawl
51. notch, pawl retaining
52. finger hole
53. side index pin placement, sheath
54. one shot/thumb press housing
55. beam of thumb press
56. groove, alignment, safety sheath
57. groove in trochar to guide to proper aim
58. sensor button
59. ram
60. guide, support ram
61. ball race, guide
62. ball race, sensor
63. spring, sensor
64. balls
65. pivot pins, force multiplying levers
66. semi-circular cam
67. hole in locking vane
68. curve in trochar
69. bore hole in receiver 70 hose barb
71 hole in ram wall for ball
72 target center hole
73 block/lever connecting pin
74 crank journals, a and b
75 tissue flap
76 alignment mark
77 fastening points for 1-2 vane

SUMMARY

This invention is the first hardware to satisfy the need for a safe trochar and a guide to install the trochar. The trochar has a safety sheath protecting the sharp point when received in the operating room, but unlike earlier hardware, this safety sheath is not removable by OR personnel. The safety sheath will protect a number of different trochar point designs. The safety sheath receives the trochar as the point exits the patient's soft tissue. The safety guide of this hardware reduces physical effort, and protects operating room personnel from cuts and sticks from the trochar. This hardware backs up soft tissue to enhance tissue piercing and further provides absolute knowledge of the direction and location of the trochar through soft tissue. The receiver on the guide is pivoted to allow ergonomic use in several tasks, including the pulling of tubing through tissue. The safety trochar is locked into the guide and may not be removed until the sharp point is locked into the safety sheath. The hardware of this invention requires no additional time, nor effort, by Operating Room personnel.

DESCRIPTION OF INVENTION, FIGS. 1-23

FIG. 1 shows an isometric view of the hardware of this invention. The trochar is held in the safety guide. There are three main sub-assemblies, the trochar (1), and on the guide, the receiver mechanism (2), and the holder mechanism (3). The receiver and holder mechanisms are slidably joined together, supported and aligned by a guide beam (4). On the receiver mechanism standard (14) is a target (5) with a center hole (72). The sharp pointed end (the first end) (6) of the trochar is pointed toward the center hole of the target. A drain tube (7) may be appended to the other end (the second end) of the trochar. The trochar is releasably held in the holder mechanism by a plurality of holder element levers, two of which are shown as (8). A resetting lever (9) serves to reset several sub-systems, as described below. Two handles, (10a and 10b) provide grip and control of the guide. These handles have finger holes, (47) and (52). A thumb press bar (12) affects the release of the trochar (1) from the safety sheath (see FIG. 2 number 13) which is enclosed inside the receiver (11). The trochar may be released from the safety sheath only under certain conditions, consistent with safety.

Figure 2:
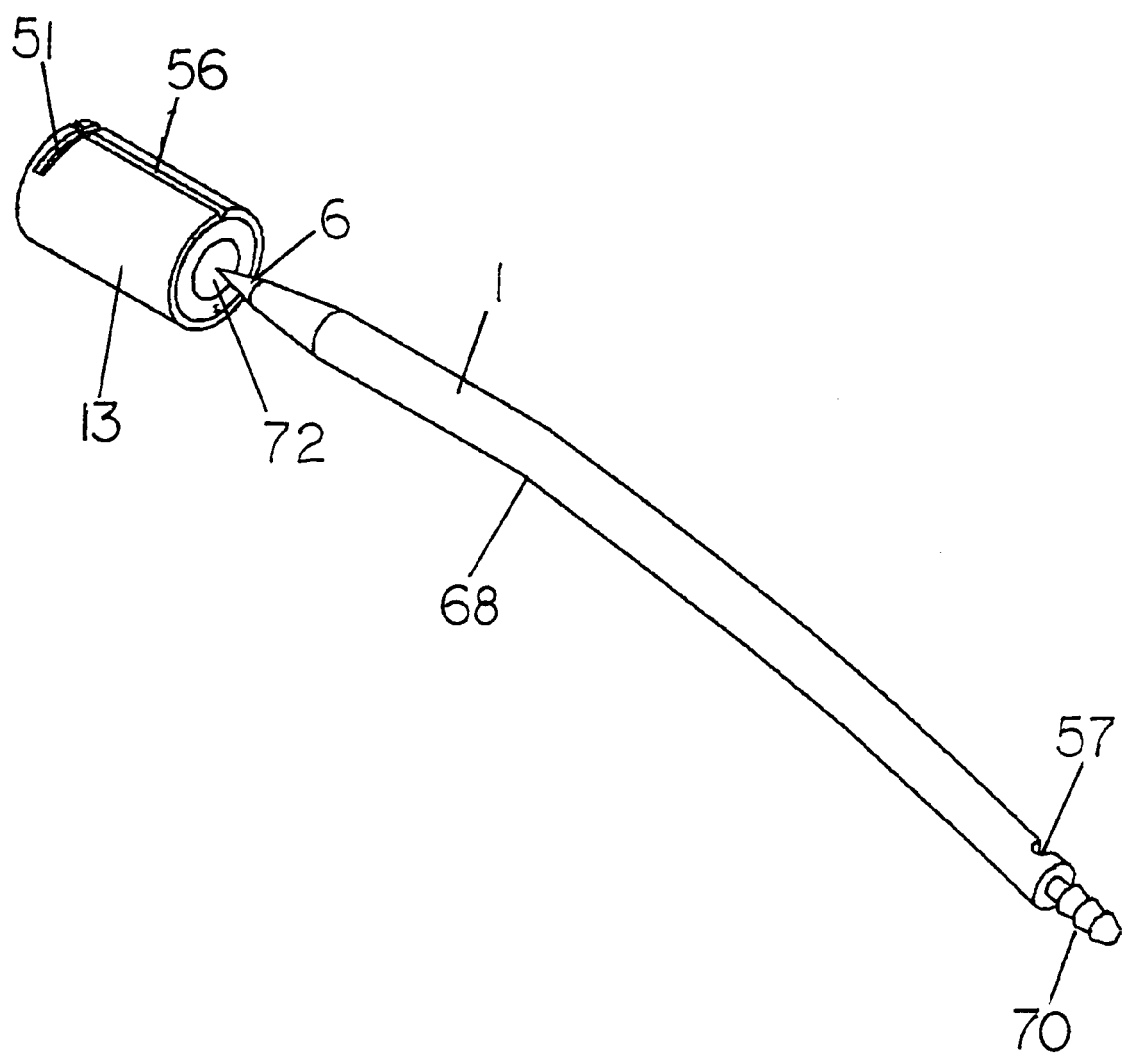
FIG. 2 shows an isometric view of a trochar aimed at a safety sheath.

FIG. 2 shows the trochar (1) partially removed and directed into the safety sheath (13). On the safety sheath is a notch (51) that serves to catch a pawl and retain the safety sheath within the receiver. On the outside diameter of the safety sheath is an alignment groove (56) for aligning the safety sheath as it is inserted into the receiver. In the center of the safety sheath is a hole (72). In FIG. 2, at the first end of the trochar is the sharp point (6). Note that there is a curve in this trochar, designated by (68). This curve defines a plane. At the second end of the trochar is a groove (57) on the diameter which groove is linear with the plane of the curve (68). At the second end of the trochar is a smaller, ribbed portion (70), the "hose barb".

Figure 3:
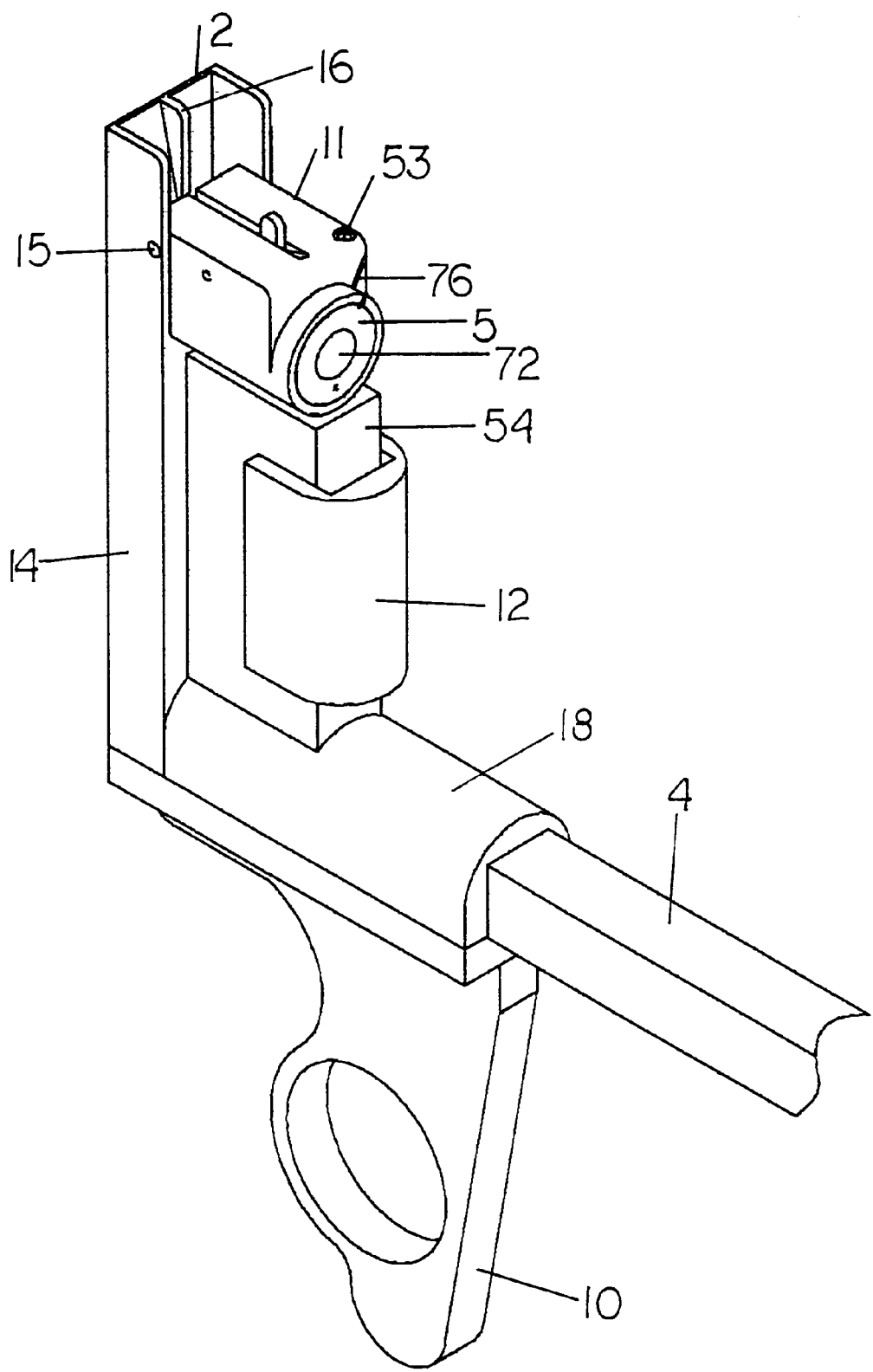
FIG. 3 shows an isometric view of the receiver section of the safety guide, with some details.
Figure 10:
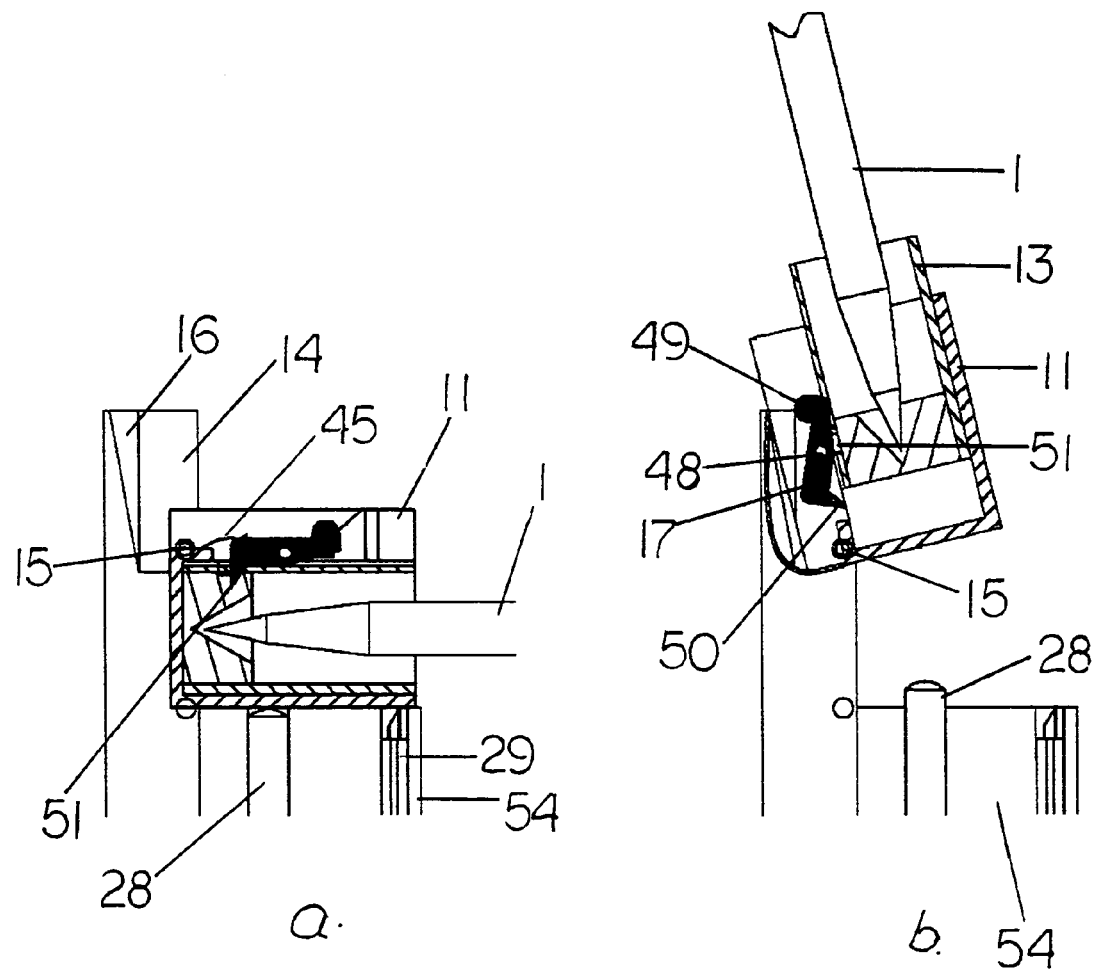
FIG. 10 (a and b) shows the action of the sheath retaining pawl, (a) is active and (b) is inactive.

FIG. 3 shows an isometric view of the receiver mechanism. The receiver (11) has a bore-hole [see FIG. 12, (69)], just adequate in diameter and length, for admitting the full length of the safety sheath. An alignment mark (76) is etched into the face of the receiver, and serves to indicate the correct orientation of the sheath for insertion. This mark is associated with the alignment pin placement (53). The receiver is pivoted on a pin (15) that is inserted through the two side flanges on the receiver standard (14). The degree of angle through which the receiver may be rotated is somewhat greater than a quarter of a full circle, approximately 100 degrees. Please refer to FIG. 10, wherein the following descriptions are clarified. Between the two flanges is a ridge vane (16) that serves to actuate the sheath-retaining pawl (17). The sheath retaining pawl (17) holds the sheath within the receiver. The sheath is released from the receiver only when the receiver is angled about the pivot pin (15) to the maximum angle, as described earlier in this paragraph. The nose (50) of the pawl, as shown in FIG. 10(b), is forced by spring (45) into a notch [FIG. 2 (51)] in the sheath housing (13). This is easy to understand as "tail (49) high, (FIG. 10a) nose (49) low (FIG. 10b) attitude." The pawl is normally "nose low", locking the sheath into the receiver, unless forced to rotate "nose high", "tail low", by action of the ridge vane (16). This action is accomplished by rotating the receiver (11) somewhat more than a quarter of a complete rotation, about pivot (15). Please note in FIG. 10(b), that at the maximum degree of rotation of the receiver, the ridge vane forces the tail of the pawl down. Forcing the tail down rotates the nose of the pawl upward, out of the groove (51) in the sheath, thus releasing the sheath from bore hole in the receiver. At this point, the trochar with the safety sheath attached, slides easily out of the receiver, as shown in FIG. 10(b).

Figure 4:
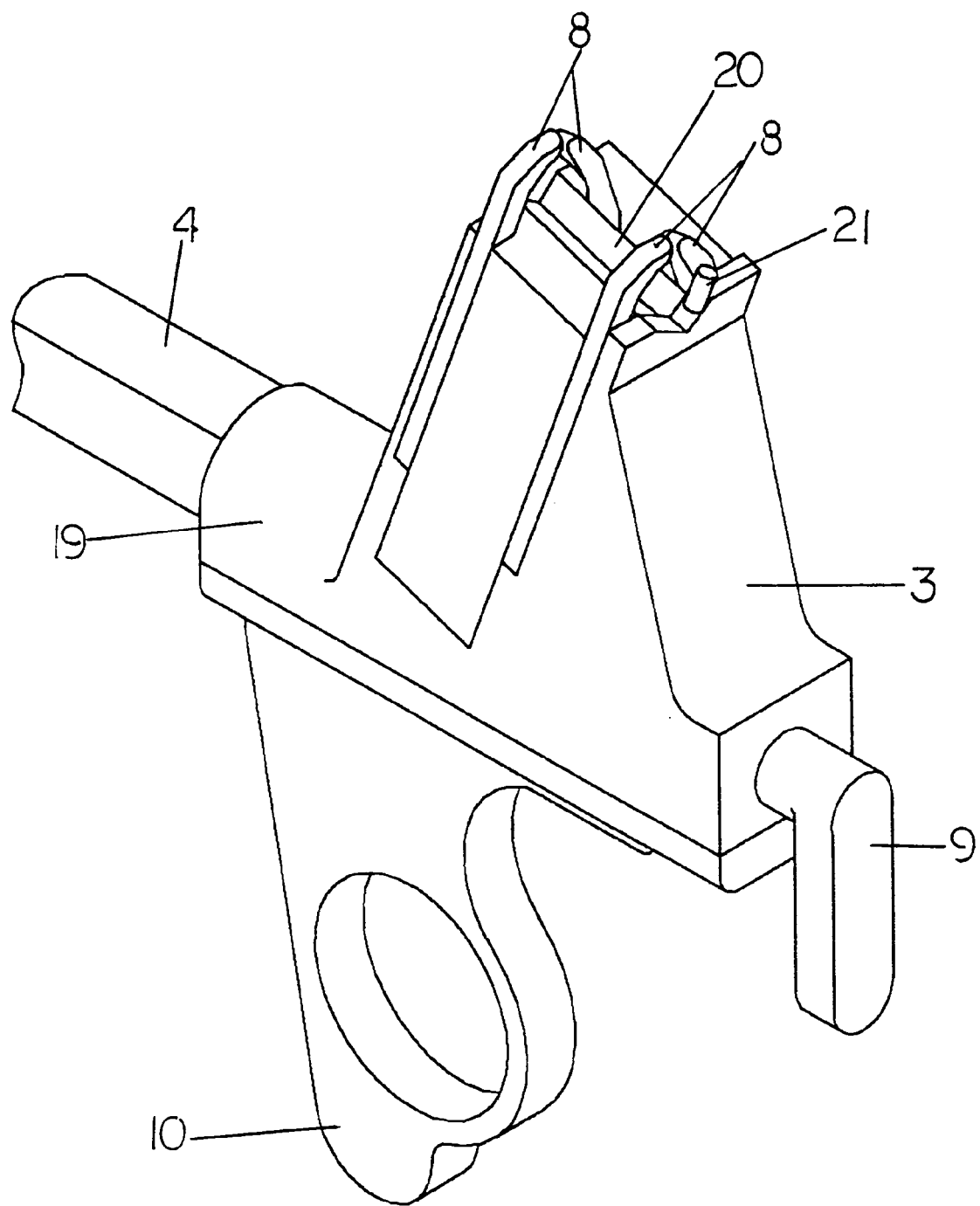
FIG. 4 shows an isometric view of the holder section of the safety guide, with some details.

FIG. 4 shows an isometric view of the holder mechanism. In this view, the elements (8) are shown clearly. These elements clamp the trochar into the "V" groove (20). A pin ward (21) is clearly shown coming up from the body (3) of the holder. A very detailed description of the holder mechanism follows below.

FIG. 5(a) and (b) show a cross section of the safety sheath. Refer to FIG. 5(a) to see the mechanism components. The trochar (1) is adjacent to and directed toward the opening of the safety sheath. The face of the sheath (the target) (5) is round and is made of light reflecting material. There is a round hole (72) in the center of the face, and the combination of a reflecting circle with a black center suggests a target. The sharp point (6) of the trochar fits into this hole and is locked therein. The safety sheath housing (25) contains several components. Number (22) is the locking vane. The locking vane is acted upon by a spring (24), which pushes the vane against the inside of the first end (5) endplate of the housing, described above as "the face". The inside of this endplate is thicker at the upper portion of its diameter than that at the diametrically opposite, lower portion. The difference in thickness is linear across the plate and the thickness gradation results in the inside wall of the housing being at an angle of greater than 90 degrees to the linear axis of the sheath housing. The locking vane is spring loaded against the inside of end plate. The locking vane has a center hole, (67) concentric with the outer diameter and the hole is only large enough to accept the diameter of the trochar (1). FIG. 5(b) shows a cutaway view of the same safety sheath; but in this view, the trochar is fully inserted into the safety sheath. Note that with the trochar inserted through the hole in the first end plate, thence through the hole in the locking vane (22) and finally into the conical concavity (26) in the second end plate, the locking vane is now shown as (27) and is labeled "locked vane". The locked vane is substantially at a 90 degree angle to the axis of the trochar, which is co-axial with the safety sheath. Because of the unsupported spring force against the lower edge of the locking vane, the trochar is locked into the safety sheath and it is not possible to withdraw the trochar without first supporting the lower edge of the locking vane by the key, FIG. 6 (29).

Looking again at FIG. 10(b), the receiver (11) is in the "up" vertical position. It is pivoted by the pin (15). In the receiver "up" position, the receiver "down" indicator button is pushed upward by a spring. When rotated clockwise to a horizontal position, as shown in FIG. 10(a) the receiver rests upon the one-shot/thumb press housing (54). In the horizontal position, the receiver (11) pushes the receiver position indicator button down, as shown in FIG. 10(a).

Figure 5:
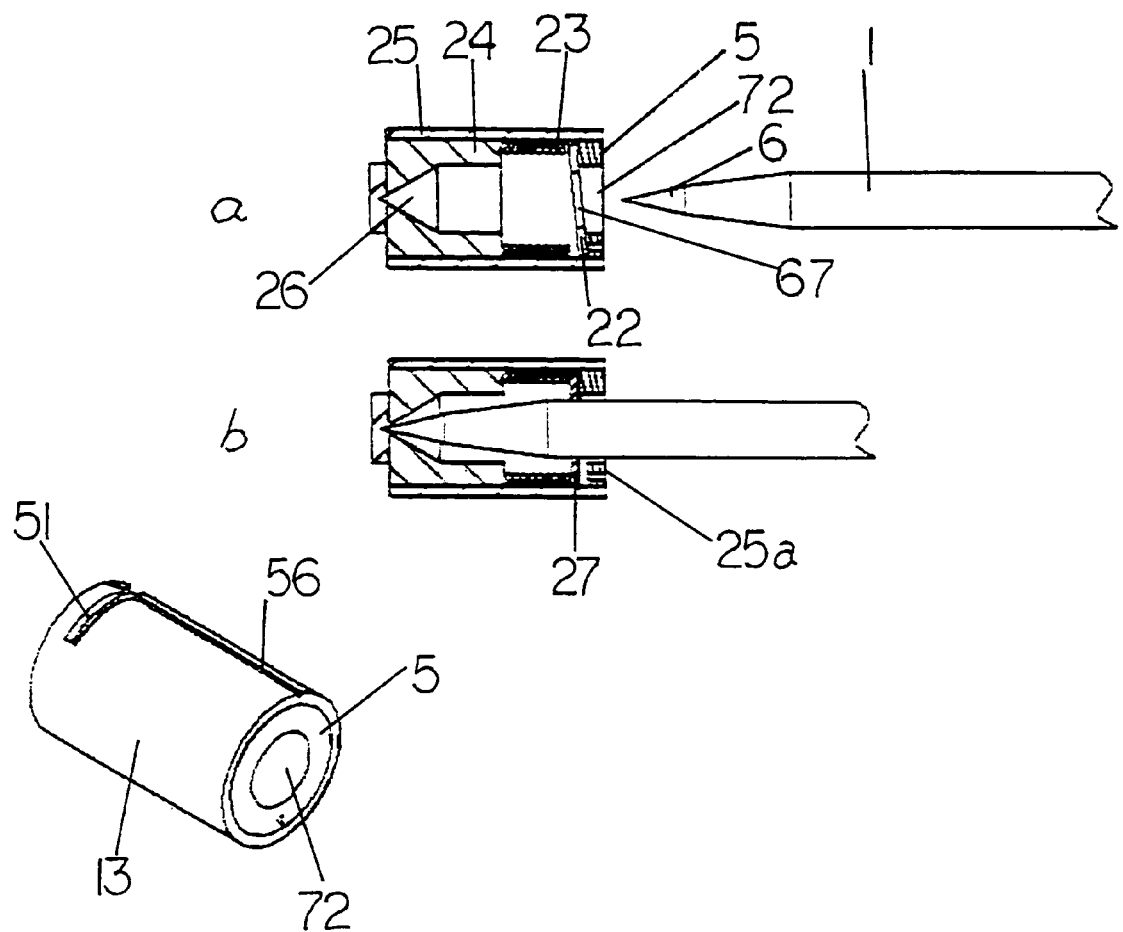
FIG. 5 shows details of a trochar adjacent to two cut-away sections, a and b, of a safety sheath.
Figure 6:
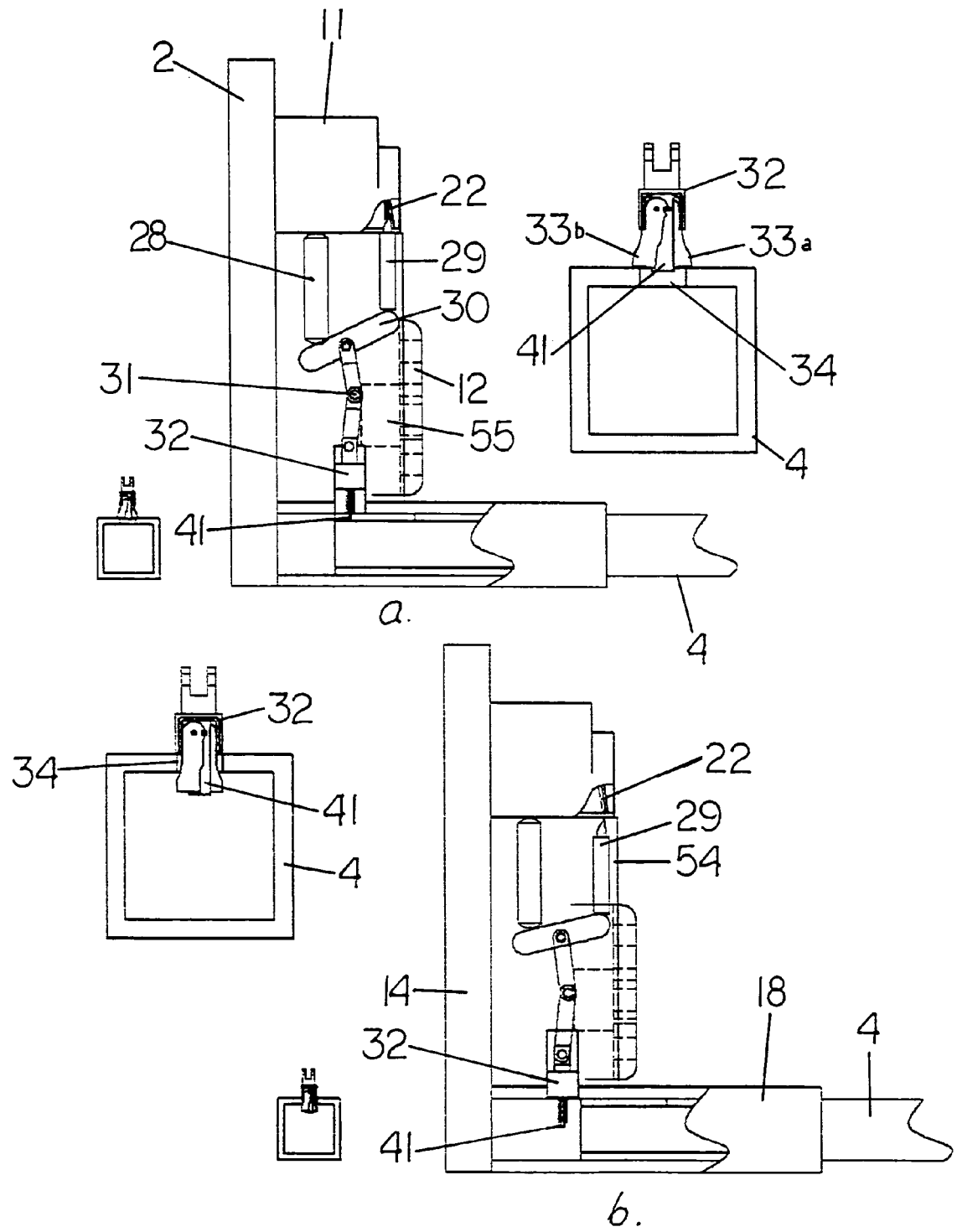
FIG. 6 shows a cutaway view with details of the "one shot" release system for the safety sheath.
Figure 8:
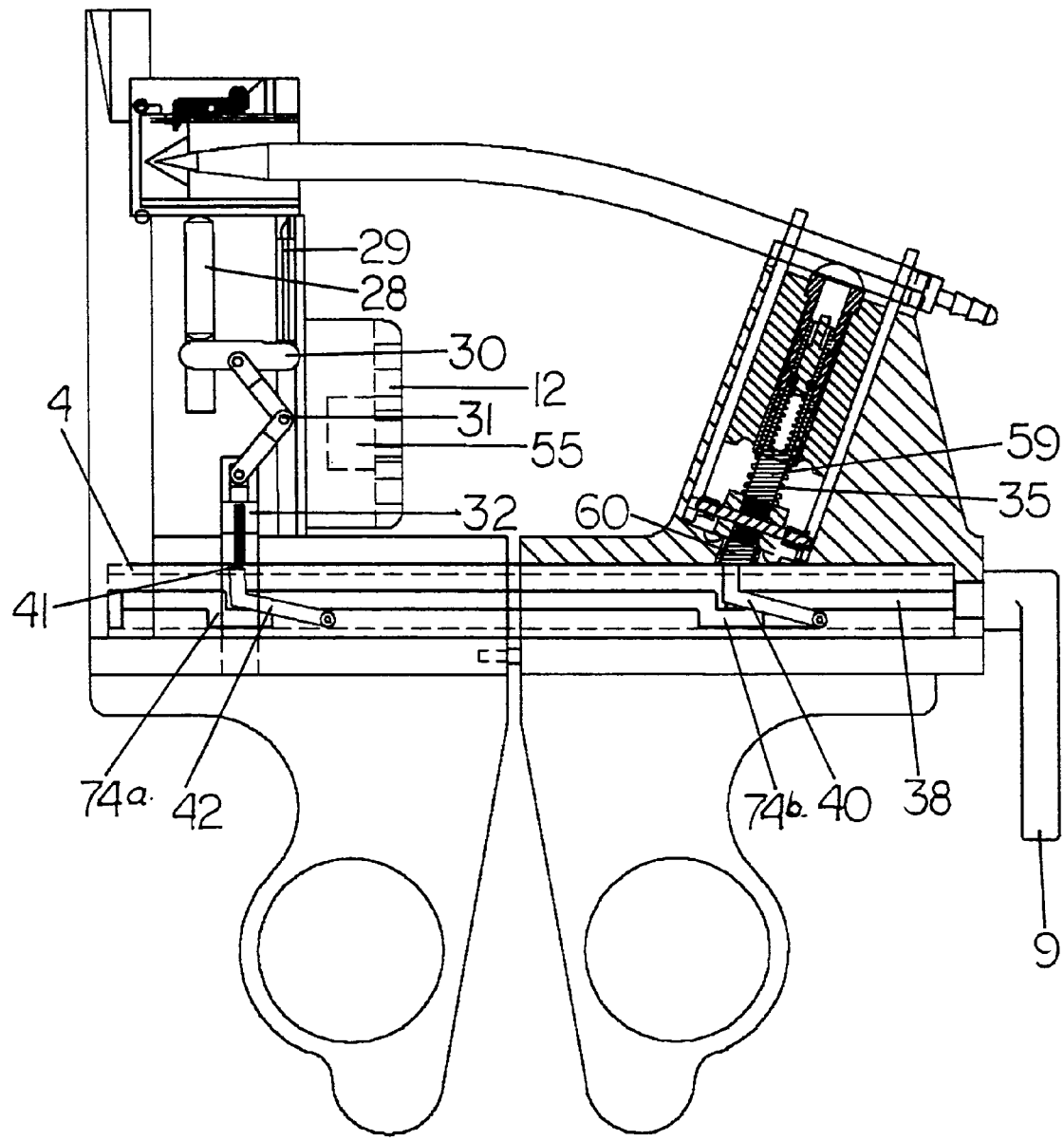
FIG. 8 shows a side view of the safety guide and trochar with cutaways of the reset mechanism.

FIG. 6 shows several cutaway views of the "one-shot" mechanism. The base of the receiver (11) forces the position indicator button (28) down when the receiver is in a horizontal position as shown in FIGS. 3 and 6. In the "down" position, this indicator button acts to push down the left end of the and/or beam (30). This is shown clearly in FIG. 6(b). The and/or beam is pivoted on the top segment of the crickle (31). Please refer to FIG. 8, to see a cutaway view of the crickle shown "broken"—that is, the upper link and lower link are not in a straight line. In FIG. 8, key (29) is shown "down" (inactive) because the beam (55) of thumb press bar (12) is not pushing the crickle into a straight line. In FIG. 6, note that key (29) has a wedge at the first end, closest to the top of the one shot/thumb press housing. In FIG. 6(b), the and/or beam is rotated upward on the right end, this action pushing up the key. The key, when "up" (active), acts upon the locking vane (22), the face of the wedge pushing the locking vane into a vertical position, thereby moving it against the force of the spring (23) (FIG. 5) to 90 degrees (normal angle) to the linear axis of the trochar. At the normal angle to the trochar, the locking vane has no locking action upon the trochar, which can then be withdrawn from the safety sheath. A boot (32) is pivoted to the lower end of the lower connecting rod of the crickle. FIG. 6(b) shows the boot in the "up" position. FIG. 6(a) shows the boot in the "down" position. The boot has two feet, (33a and 33b) as shown in FIG. 6(b). Between the feet is a boot pushrod (41). The boot is "up" when supported by the beam (4), as the feet are angled apart and straddling slot (34). The inset to the right of FIG. 6 (b) shows the feet straddling the slot and supported by beam (4). FIG. 6(a) and the inset to the left shows the boot "down", with the feet together in the slot (34) of the beam (4). A thumb press bar (12) is shown in FIG. 6. This is normally in the "out" (inactive) position. From the backside of the thumb press bar (12), and communicating through a slot in the one-shot housing (54) is a beam (55). This beam may act upon (push) the crickle when the thumb press bar is pushed inward. This condition is shown in FIG. 6(b).

Figure 7:
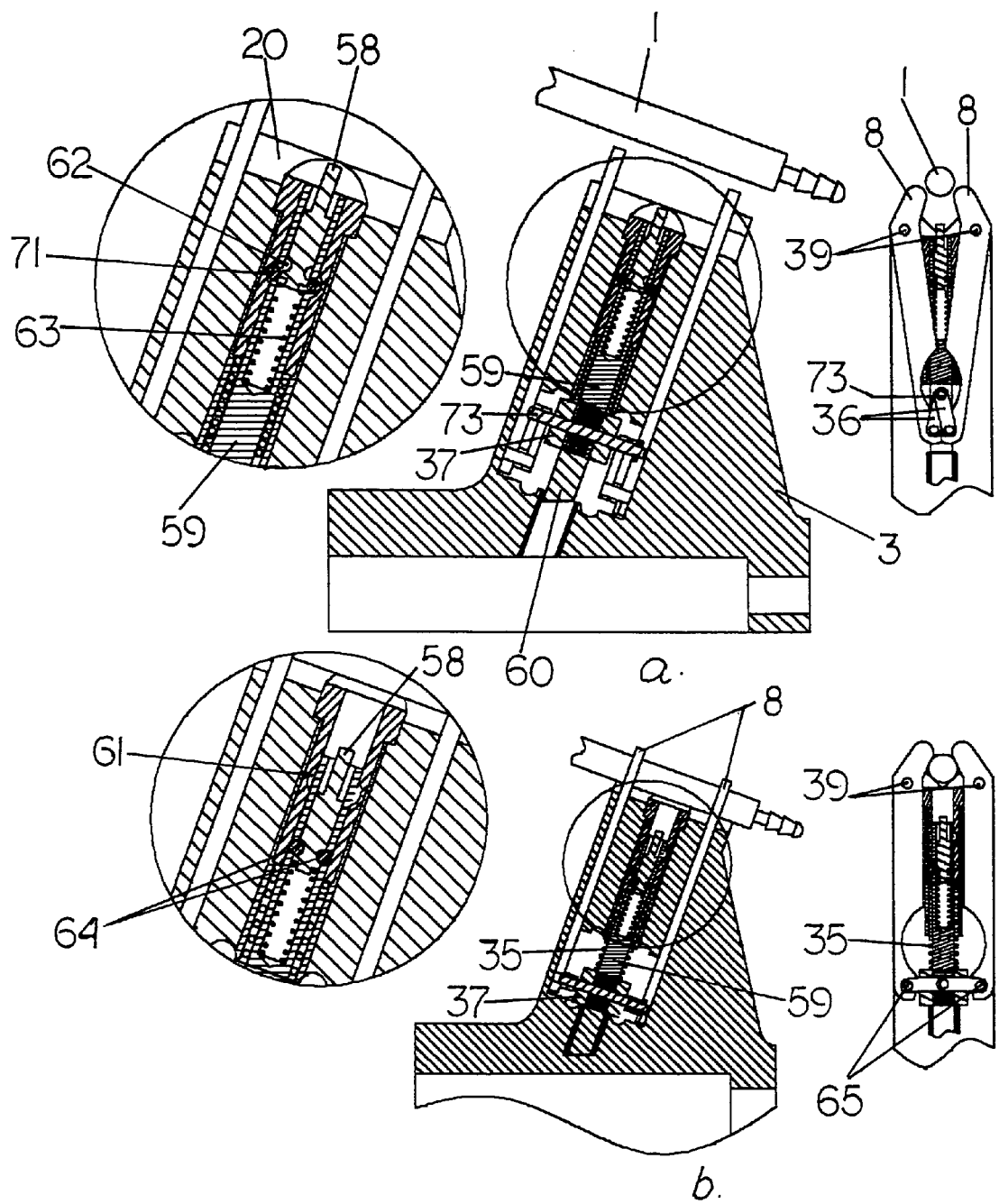
FIG. 7 shows two cutaway views with details of the holder mechanism of the safety guide.

FIG. 7 shows several views, (a and b) of the trochar holder sub-assembly. FIG. 7(a) is a side view cutaway of the holder mechanism in the "open" state. Holder mechanism body (3) is shown cut away to expose details of the mechanism. A trochar (1) is just above the elements (8) and the "V" groove (20), which runs the width of the angled top of body (3). Block (37) is in the "up" position. Below block (37) is a guide, the support guide (60) for the ram (59). To the right of this view is an end view, cut away to expose the element (8) levers in full view. Force multiplying levers (36) are at an acute angle to each other. An inset to the left of FIG. 7(a) shows an enlargement of a section of the figure. In the center of the "V" groove (20) is trochar sensor button (58). In this view, the sensor button is in the "up" position. Around the lower end of this sensor button is a groove, ball race (62). Pushing up on the sensor button is a compression spring, sensor spring (63). FIG. 7(b) is a cutaway of the side view of the holder with the trochar "closed", locked into position. View (b) shows the sensor button in the "down" position. Block (37) is in the down position, forced there by holder actuator spring (35). The trochar, when locked in, fits into "V" groove (20). To the right of FIG. 7(b) is an end view, cut away to show the elements. The trochar (1) is locked into the "V" groove by the action of the first end of elements (8). At the second end of elements (8) are pivots (65) a and b. These pivots attach force multiplying levers (36) to the second end of the elements. In this view, the force multiplying levers are in an almost straight line. The elements (8) are forcing the trochar down, and therefore holding it into the "V" groove. To the right of FIG. 7(b) is an inset, an enlargement of the sensor and ram. In this view, the sensor is in the "down" position, held there by balls (64). The balls are shown more clearly as being in the sensor ball race (62) and holes (71) through the wall of the ram. Ram (59) is also down, forced by spring (35), as described above.

FIG. 8 shows a side view of the reset mechanism. This mechanism is housed inside the support and alignment beam (4). A torsion rod (38) may be rotated by lever (9). The torsion rod is supported at the first end by a bearing in the holder housing base (3). On the torsion rod are two cams, (79a and 79b). Rotating reset lever (9) one full turn, actuates cams (74a and b) against jack (40) and jack (42) respectively. Jack (40) pushes up on support ram guide (60) against block (37) resisted by spring (35). Jack (42) pushes up on boot push rod (41). The pushing up of these elements serves to reset the holder and one-shot mechanisms.

Figure 9:
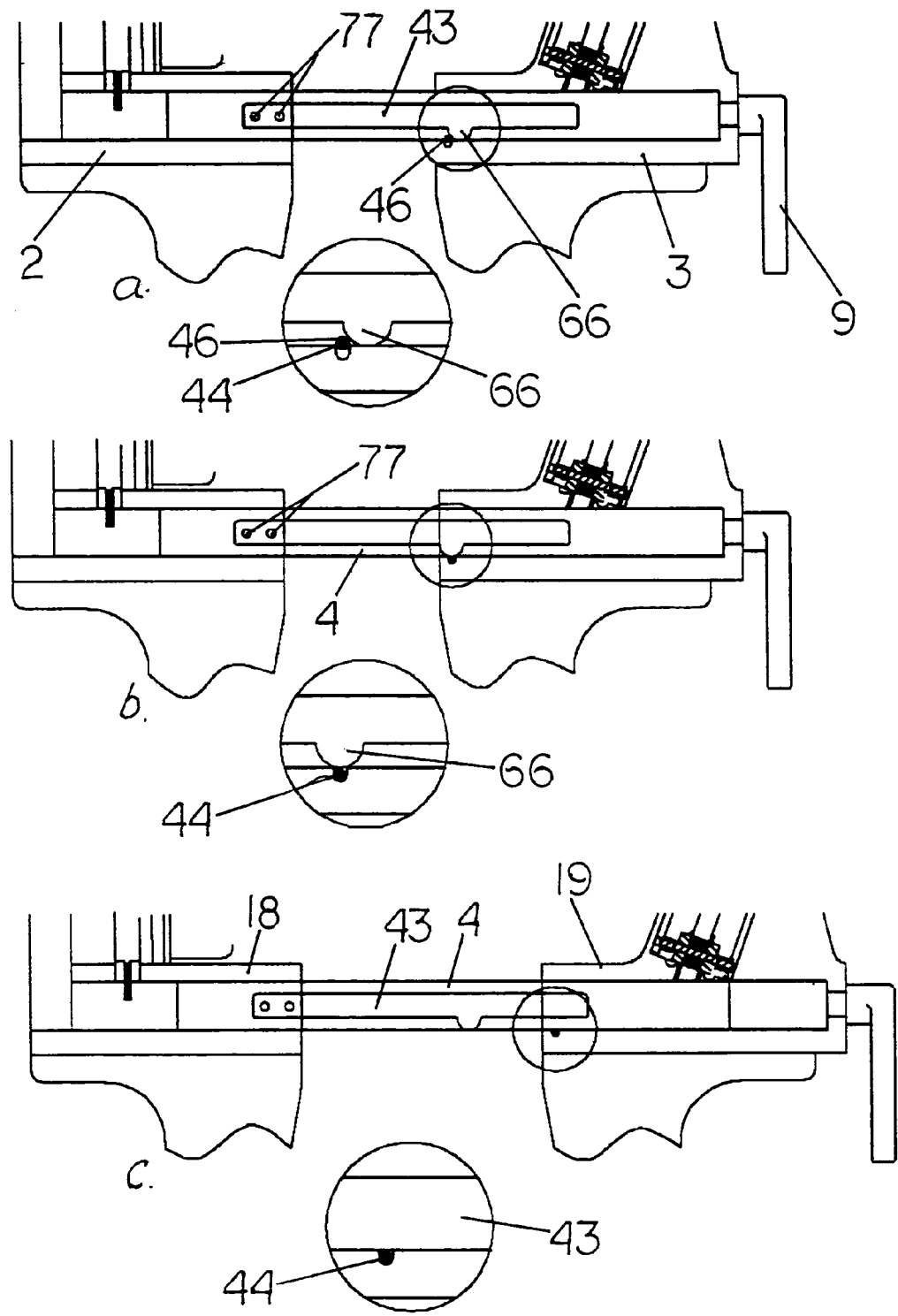
FIG. 9 shows three side views, a, b, c, with cutaways of the 1-2 extension control mechanism, and with three insets enlarged and cut away for details.

FIG. 9 shows cut away sections of three side views (a, b, c) of the 1-2 extension control mechanism. To affect the priority of the receiver mechanism, shown in FIG. 1, (2) and FIG. 9 (2) with carriage (18) over that of the holder mechanism FIG. 1 (3) and FIG. 9 (3) with carriage (19), an extension control is incorporated into the safety guide. A lock groove (46) is incorporated in the support and alignment beam (4). A pawl (44) is spring loaded, so as to maintain the pawl in the groove and therefore prevent the holder sub-assembly (3) from sliding on the beam. Held to the receiver sub-assembly by fasteners (45) is the 1-2 vane (43). At the other end, the 1-2 vane has a semi-circular cam (66). This cam acts to push down the pawl (44) and thus displace and release the pawl from the lock groove (46). FIG. 9(a) shows the receiver mechanism slid off the beam far enough for the cam (66) to contact the pawl (44) which is shown up in the groove (46). The inset below (a) is enlarged to show details. FIG. 9(b) shows the receiver mechanism slid yet further than in (a), such that the cam (66) has pushed the pawl (44) from the slot (46) which can not be seen because it is in this view covered by the cam. FIG. 9(c) shows the holder mechanism slid to the right along the beam, because the pawl (44) is free of the groove (66). In the view (c) the receiver mechanism in the same place on the beam as in (b). Because of the 1-2 extension control, the Holder will not slide on the beam until the Receiver is fully extended on the beam. This means that in opening the safety guide, the Receiver sub-assembly slides completely open before the Holder slides at all. When fully opening the safety guide, the Receiver subassembly slides first, and when it is fully extended, the Holder slides until it is fully extended.

FIG. 10 shows the action of the lock to hold the safety sheath into the receiver (11), as described above in detail.

Figure 11:
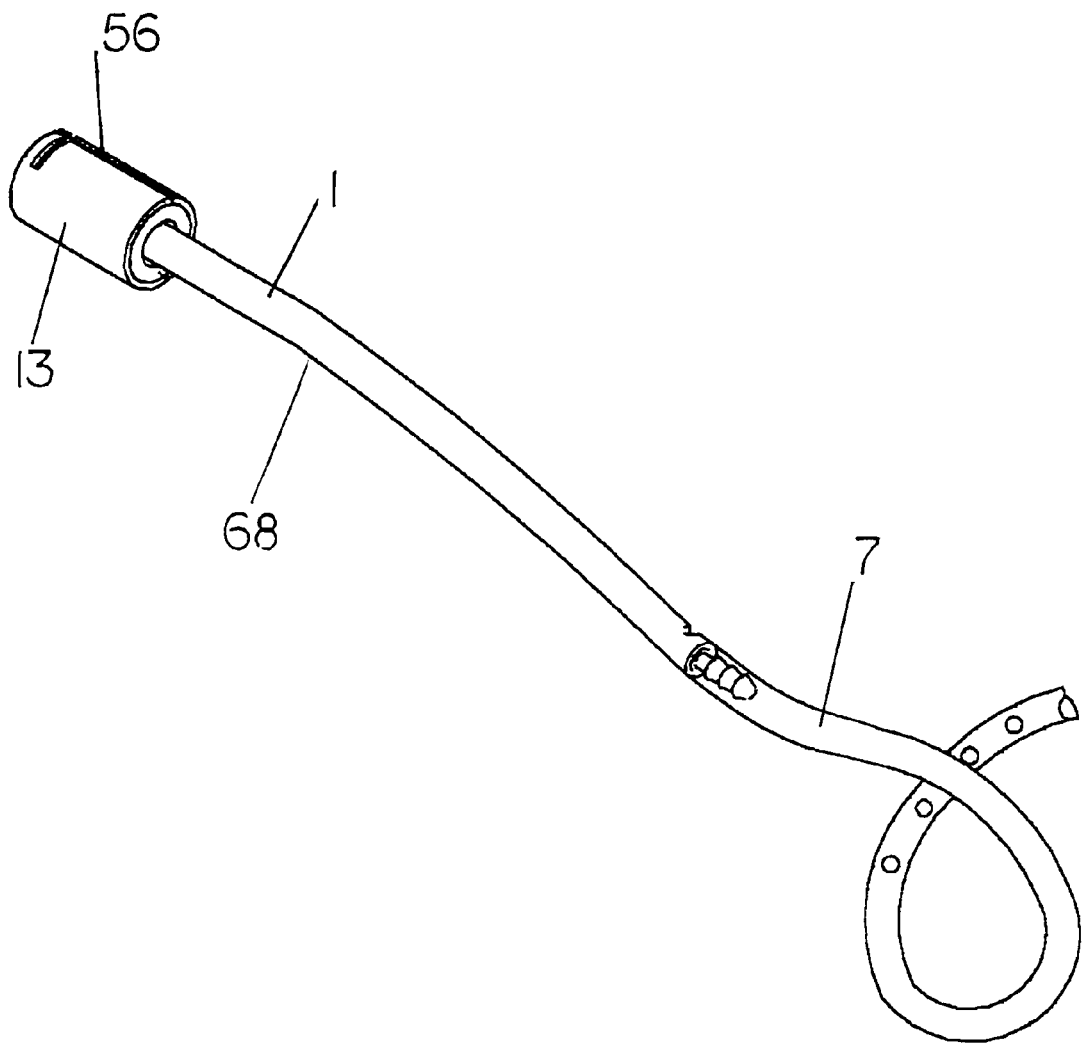
FIG. 11 shows the trochar with a tube as dropped into the sterile field of surgery, wherein the trochar sharp point is protected by the safety sheath.

FIG. 11 shows an isometric view of a trochar (1) with safety sheath (13 and tubing (7) attached to the hose barb (70). See FIG. 2. This view shown in FIG. 11 is representative of the trochar as received in surgery. Note that the safety sheath is protecting personnel from the sharp point (inside the sheath, therefore not seen in this view) of the trochar.

Figure 12:
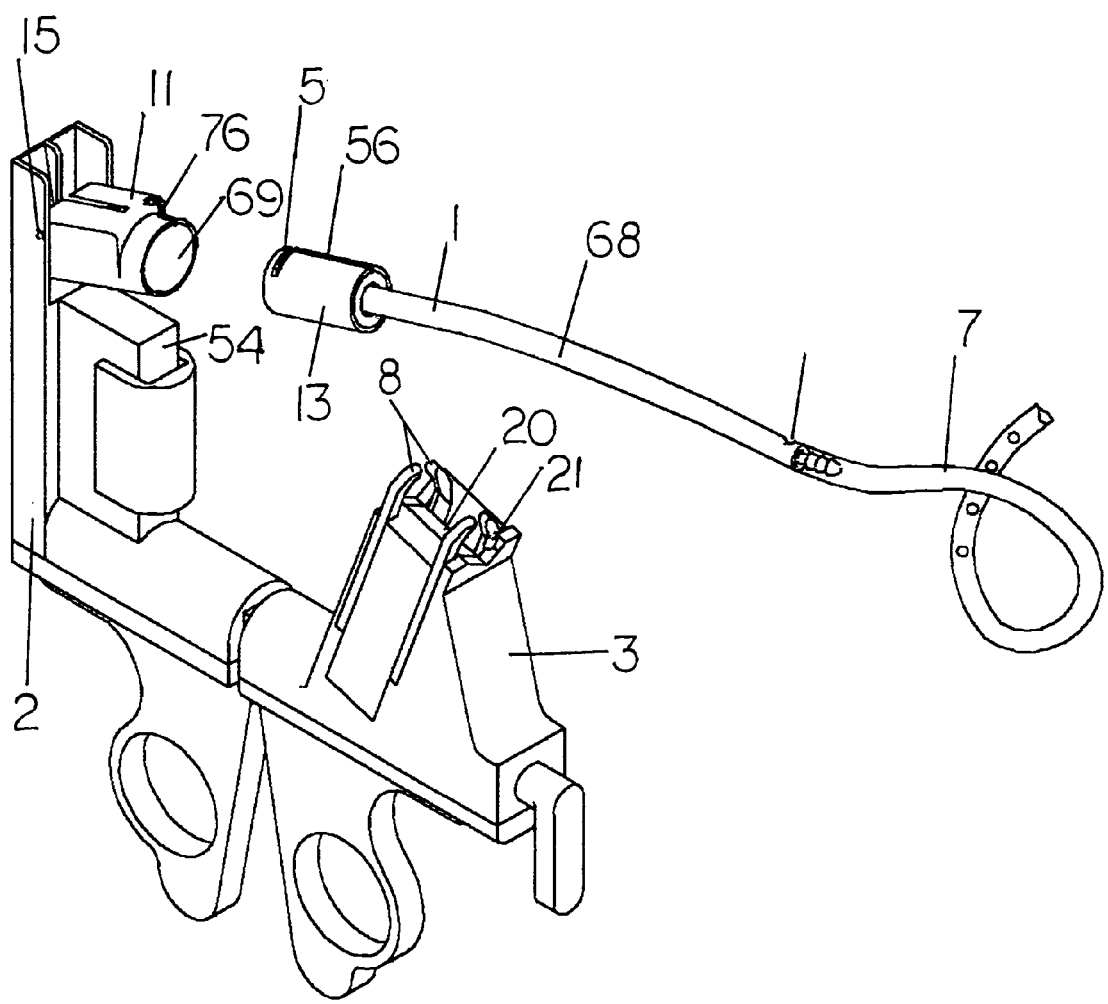
FIG. 12 shows an isometric view of the safety guide prepared to receive the trochar with safety sheath and tube.

FIG. 12 shows an isometric view of a safety guide and trochar as received into the sterile field in the OR. The receiver (11) bore hole (69) is empty and slightly angled upward. The safety sheath (13) on the trochar (1) is aligned with the bore of the receiver. Elements (8) are opened.

Figure 13:
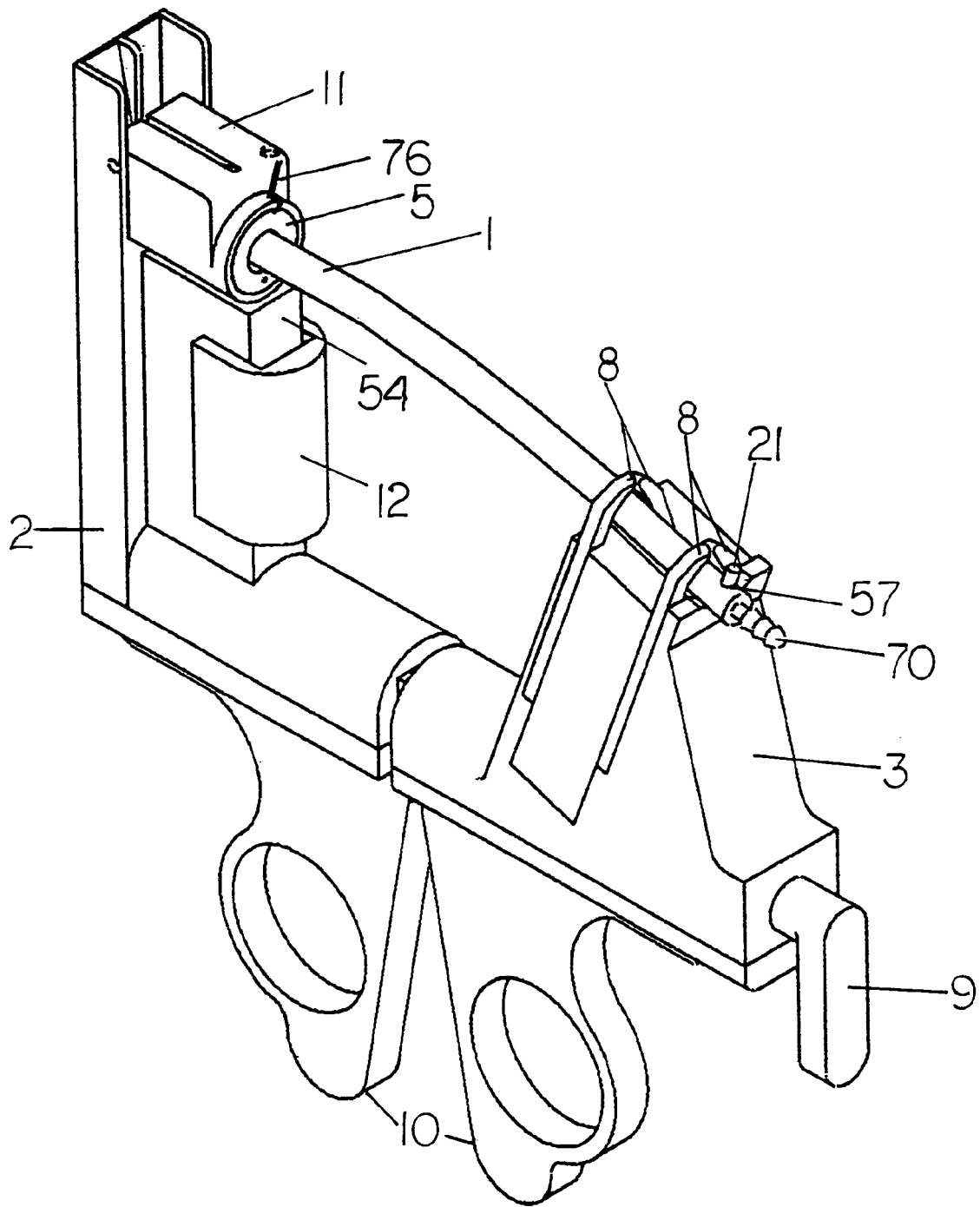
FIG. 13 shows an isometric view of the safety guide with trochar and safety sheath inserted into the receiver mechanism and locked into the holder mechanism.

FIG. 13 is an isometric view of the safety guide loaded with the trochar. The receiver (11) is horizontal and lying against the one shot/thumb press housing (54). The safety sheath face (5) can be seen in the bore hole of the receiver. The trochar (1) is down in the groove of the holder (3) where it is locked into place by the elements (8). The ward (21) is against the trochar, in slot (57). The guide is closed, with the handles (10) fully pulled together.

Figure 14:
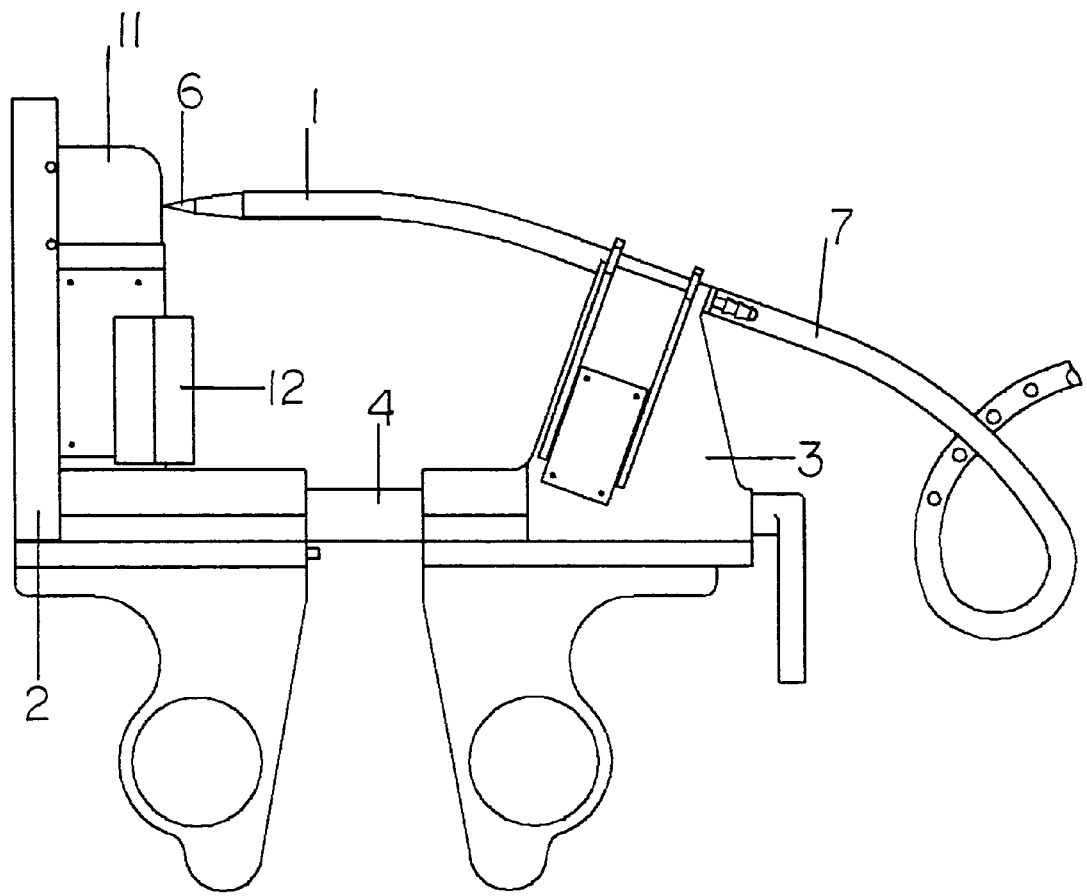
FIG. 14 shows the safety guide and trochar, wherein the guide is partially opened, just exposing to view the sharp point on the trochar.

FIG. 14 is a side view of the safety guide opened sufficiently to expose the sharp point (6) of the trochar. The beam (4) is exposed by the action of sliding the receiver mechanism (2) to the left. The holder mechanism (3) has not moved to the right, only the receiver has moved on the beam.

Figure 15:
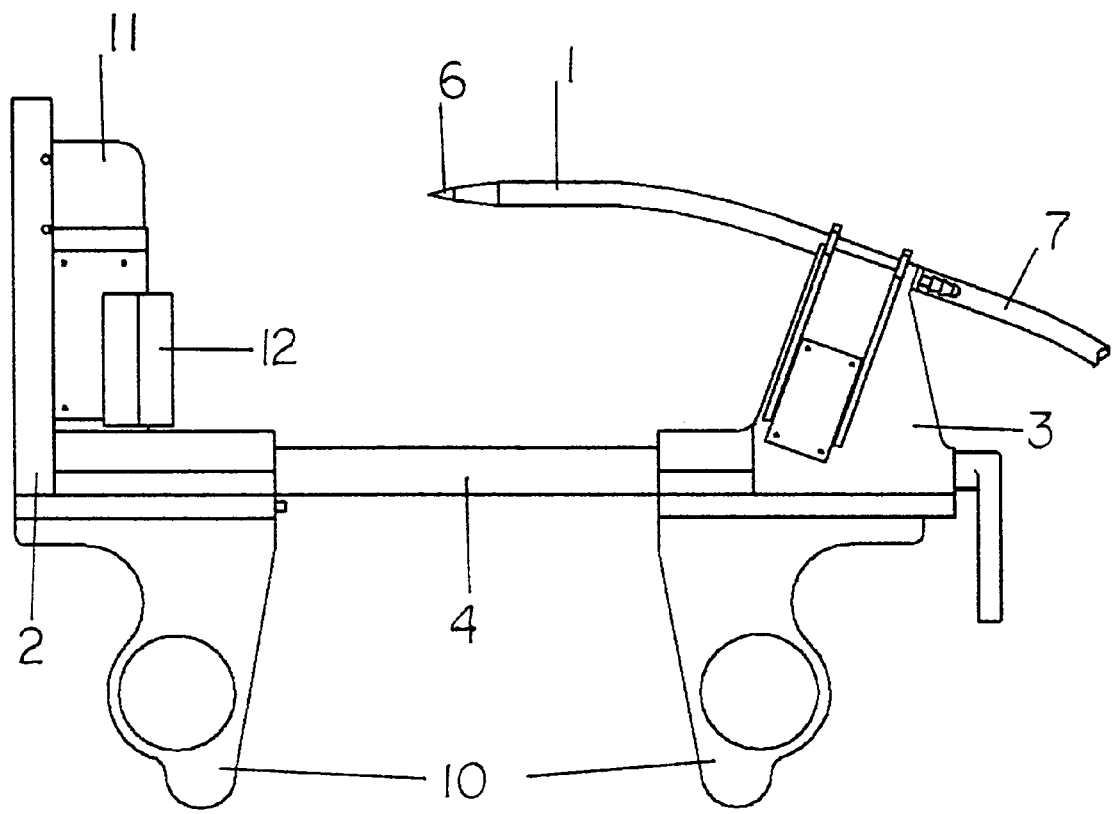
FIG. 15 shows the safety guide fully opened.

FIG. 15 shows a side view of the safety guide fully open, with the sharp point (6) being at the maximum distance from the receiver (11). A substantial length of the safety beam is seen, the receiver mechanism (2) having moved to the left (to the maximum extent) along the beam and the holder mechanism (3) having moved to the right along the beam. The handles (10) are widely spaced.

Figure 16:
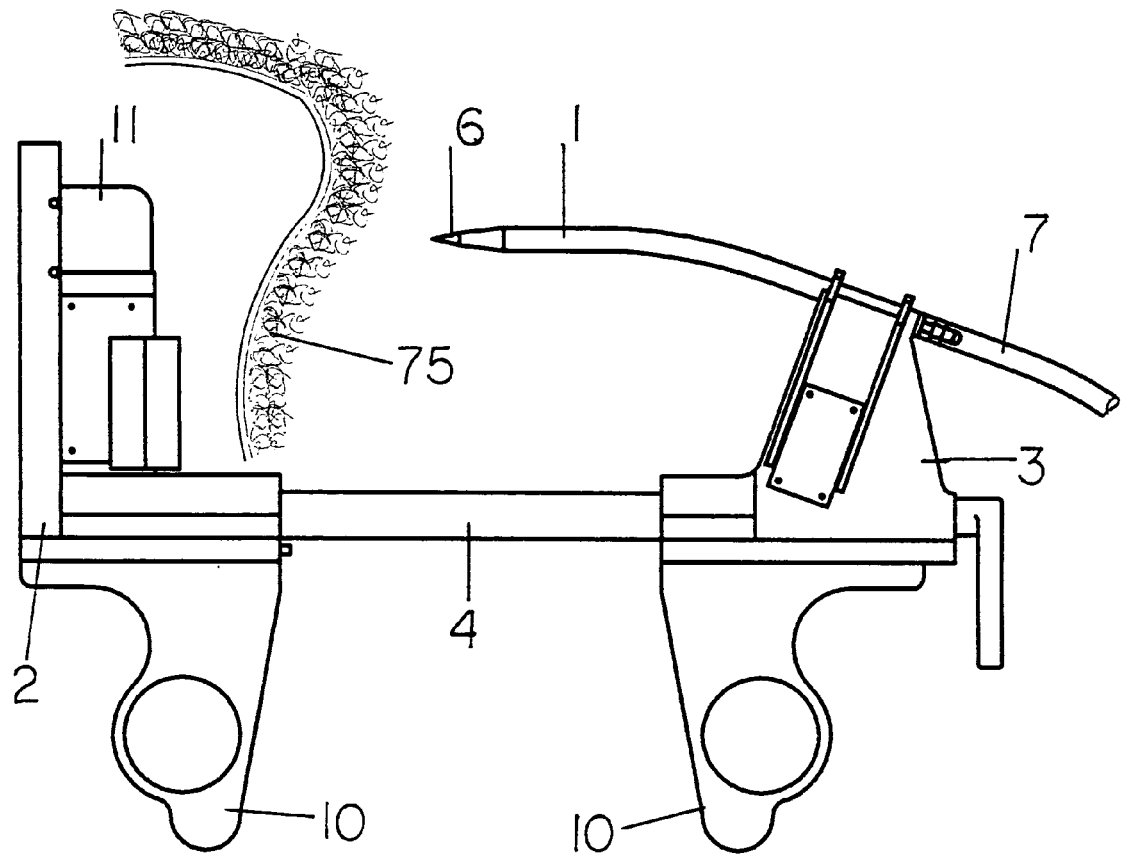
FIG. 16 shows a tissue flap inserted into the opening of the safety guide between the receiver target and the sharp point of the trochar.

FIG. 16 shows a side view of the safety guide fully open, as in FIG. 15. A tissue flap (75) is inserted between the receiver (11) and the trochar (1) sharp point (6).

Figure 17:
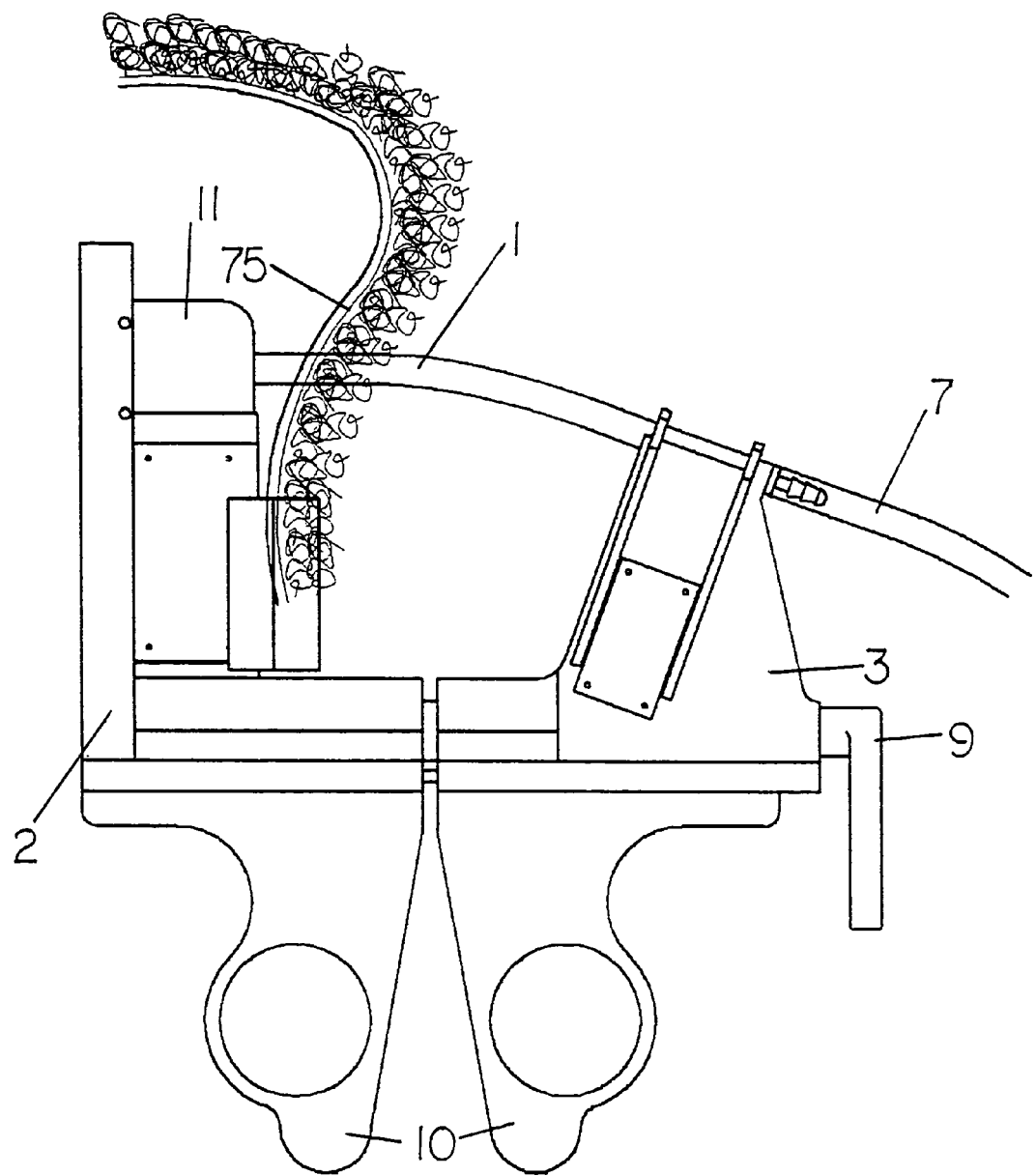
FIG. 17 shows the safety guide fully closed, the sharp point of the trochar having pierced the tissue and advanced into the safety shield within the receiver mechanism.

FIG. 17 shows a side view of the safety guide fully closed, the handles (10) being pulled together. The trochar has pierced the tissue flap (75) and the sharp point is out of view, locked into the safety sheath in the receiver (11).

Figure 18:
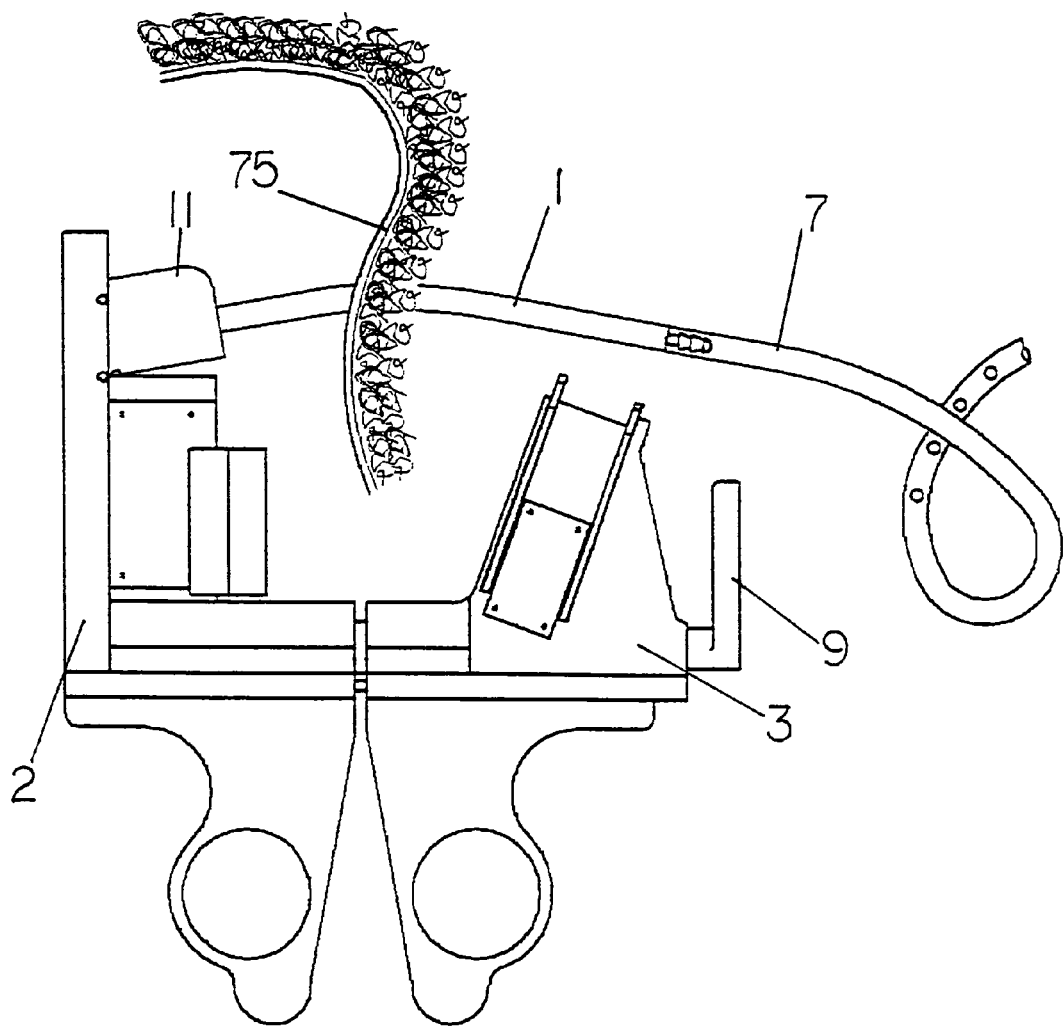
FIG. 18 is a side view of the safety guide closed and the trochar released from the holder; the elements have been opened through the action of rotating the lever to the upward position shown.

FIG. 18 is a side view of the safety guide closed and the trochar released from the holder (3). The elements (8) (see FIG. 1) have been opened through the action of rotating the lever (9) to the upward position shown. The tissue flap (75) is pierced by the trochar (1). The tube (7) is attached to the trochar.

Figure 19:
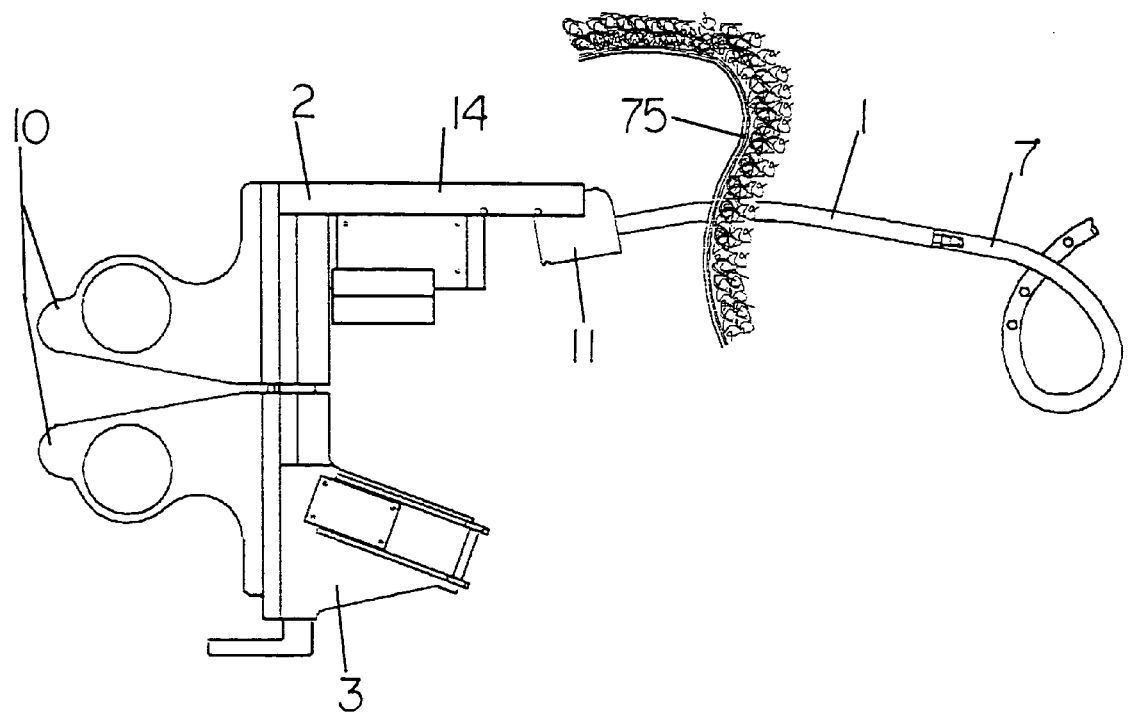
FIG. 19 shows the reset lever being rotated, and the trochar released from the holder.

FIG. 19 shows a side view of the safety guide rotated such that the receiver standard (14) is in a substantially straight line with the trochar (1) which is locked into the receiver (11). The handles (10) are together and are used to aid in pulling the guide to the left, thus drawing the trochar through the tissue flap (75).

Figure 20:
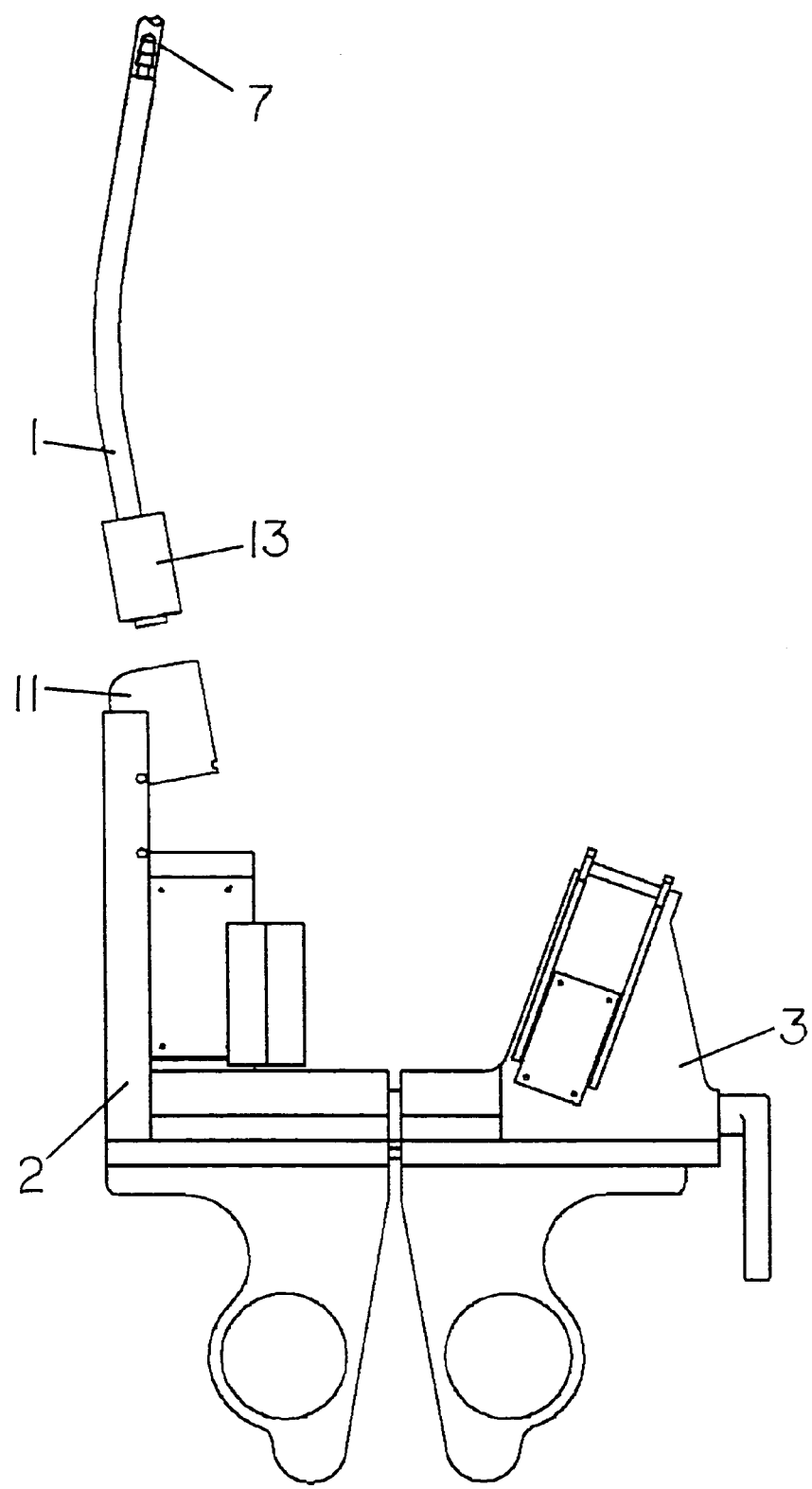
FIG. 20 shows the safety guide pulling the trochar with tube through tissue.

FIG. 20 shows a side view of the safety guide and of a trochar (1) protected by a safety sheath (13). The tube (7) is cut short close to the trochar (1), which has been pulled from the receiver (11).

Figure 21:
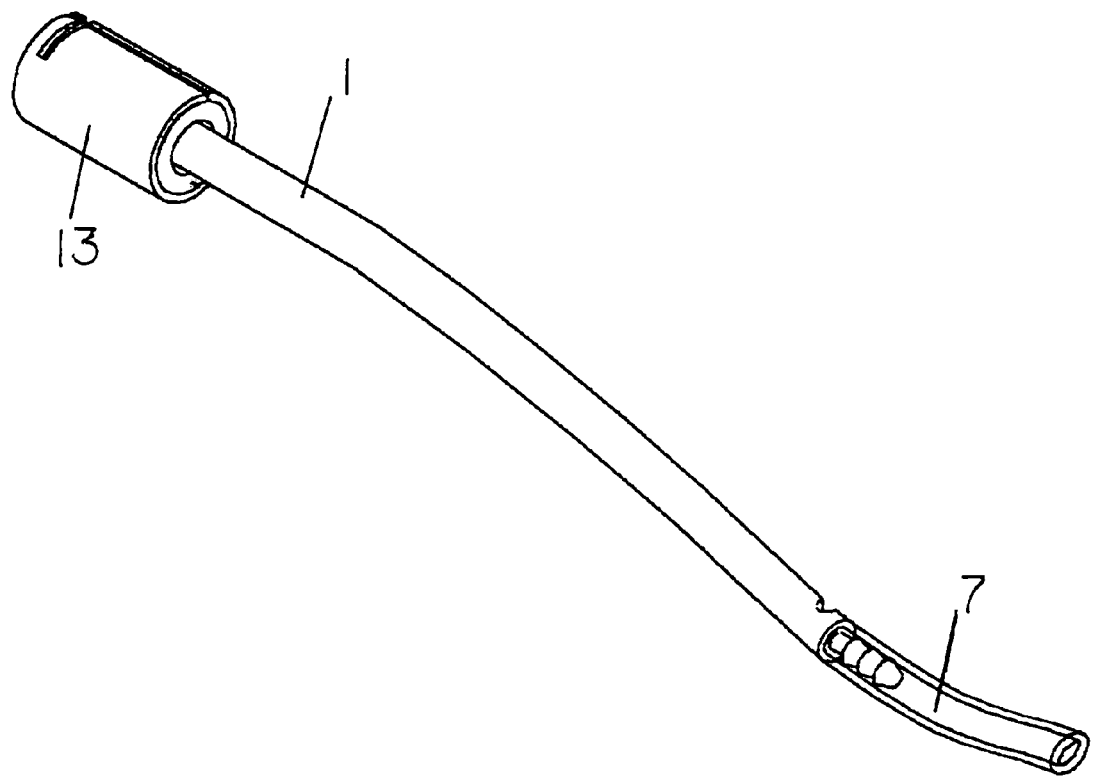
FIG. 21 shows the safety guide with trochar released and pulled from the receiver and cut free from the tube.

FIG. 21 shows an isometric view of the used trochar (1), the sharp point locked inside the sheath (13), which is covering and protecting personnel from hazardous scratches and punctures. The tube (7) is short, having been cut from the full drain tube, now in the patient.

Operation of Invention

The manner of using this safety guide for sharp instruments is simple and self-explanatory. In the preferred embodiment (FIG. 1), a trochar (1) is provided with a safety sheath (13), (see FIG. 12, #13) and means (70) for attaching a tube (7). A safety guide is provided for handling the trochar. The safety guide has three main sub-assemblies, as shown in FIG. 1. The holder (3) serves to hold and guide the trochar. The receiver sub-assembly (2) accepts and retains the safety sheath. The receiver also provides a system for releasing the trochar (1) from the safety sheath. An additional feature of the safety guide is the provision for articulating the guide so that it us useful as a handle when pulling a drain tube (7) through tissue. To facilitate opening and pulling the safety guide, handles (10) are attached to the receiver and holder sub-assemblies. Connecting the holder and receiver sub-assemblies is a support beam (4). The holder and receiver slide on this beam so that the guide may be opened. When the guide is opened, tissue (75) can be inserted into the opening, as shown in FIG. 16. A lever (9) is provided to "re-set" the guide.

The actual sequence of use is: A trochar with sheath is inserted into the safety guide. The guide is opened, separating the trochar from the target. Tissue is inserted into the opening and the guide closed. The trochar second end is released from the holder and using the guide as a handle, the tubing is pulled into the proper position in the body. The tubing is cut and the trochar, protected by the sheath is discarded.

The above steps are presented here, below, in greater detail:
In the operating room, the trochar is dropped from a sterilized peel pouch onto a tray within the sterile field. FIG. 11 shows the trochar as received by the operating room, after removal from the peel pack and dropped onto the sterile tray. In FIG. 1, number (1) is the trochar and FIG. 11 shows the safety sheath (13) covering the sharp point (6) on the first end of the trochar. A drain tube is shown as number (7). This drain tube is attached to the trochar over a hose barb (70) on the second end of the trochar. The trochar is typically curved, (68) between the first and second ends. A groove (57) across the diameter of the trochar at the second end is co-axial with the plane of the curve (68) and so this groove (57) serves to "index" the trochar over ward (21). Therefore, the direction of the point (6) (around the curve) is known. For reference, FIG. 2 shows a trochar removed from the sheath. The sheath is not removable by pulling on it. To remove the safety sheath, so as to expose sharp pointed end of the trochar, the trochar with sheath is installed into the safety guide. See FIG. 12. Holding the trochar (1) with the curve (68) upward and therefore with the crown away from the safety guide, direct the safety sheath (13) into the bore (69) in the receiver (11). Inserting the safety sheath into the receiver is straightforward, requiring only that the alignment groove (56) is aligned with the alignment mark (76) on the face of the receiver. Push the trochar assembly fully into the receiver. When fully inserted, the safety sheath is locked into the receiver by the action of the pawl (17). The nose (50) of the pawl drops into the notch (51). See FIG. 10. The receiver (11) is pivoted on pin (15). Next, swing the trochar second end down into the holder into the "V" groove (20). Since the trochar is locked into the safety sheath and the safety sheath is locked into the receiver, the three parts swing together as an assembly around pivot (15). As the trochar enters the "V" groove (20) in FIG. 4 it will pass between the elements (8). FIG. 2 shows the trochar and sheath in detail. The lateral groove (57) in the trochar second end, passes the ward (21) alongside the "V" groove and guides the trochar straight down. See FIG. 4, also. The ward fits snugly in the straight, lateral groove, and therefore, the trochar is indexed to the proper rotation and the curve (68) is in the same plane as the vertical plane of the safety guide. A trochar sensor button (FIG. 7) (58) is located in the center of the "V" groove. When the trochar touches this button, the elements (8) close onto the trochar, forcing it into intimate contact with the "V" groove. The trochar is tightly locked into position by the action of the elements and may not move in any direction. Additionally, the trochar point is aimed straight at the target in the receiver. Refer to FIG. 1.

The clamping action of the elements is explained as follows: Refer to FIG. 4, which shows the holder sub-assembly (3). "V" groove (20) receives the trochar. Elements (8) close upon the trochar as shown in FIG. 1. FIG. 7 shows a cutaway view of the holder sub-assembly. The elements are shown completely exposed in the two cutaway end views to the right side of FIG. 7. The first end of the elements (8) are pivoted around pins (39). The second ends of elements (8) are attached to the second ends of levers (36) by pivot pins (65). The first ends of levers (36) are attached to block (37) by block/lever connecting pin (73). The block (37) is retained in the "up" position against holder actuator spring (35) by the sub-assembly shown in FIG. 7. The holder assembly consists of the four holder elements (8) which, as described more fully above, apply force upon the trochar and hold it in the groove (20). Without a trochar in the groove, the sensor button (58) is in the "up" position, therein retained by the sensor spring (63). In this "up" position, the balls (64) are held in the larger radius groove, the guide ball race (61). Being in the guide ball race and holes (71) in ram wall, the balls lock the support ram (59) in the "up" or "unload" position against spring (35). When the trochar is inserted into the "V" groove (20), the sensor button (58) is pushed to the "down" position. This causes the sensor ball race (62) to line up with the balls (64). When the ball race aligns with the balls, the balls flow into this smaller race (62), and therefore the ram (59) is unlocked and travels down under spring (35) force, as does the block (37). The block (37) is connected with the ram, and as it travels down, the block acts upon the actuator levers (36a and b) through pin (73). This in turn causes the second end of element levers (8) to move outward, forcing element first ends to move inward towards one another, and therefore to clamp on and push down the trochar and hold it into the "V" groove. It will be appreciated that the lever-arm advantages and angular advantages result in significantly high clamping forces upon the trochar. These forces prevent the trochar from moving in any direction. It is fixed in X, Y and Z. The rotational direction, "Theta", is prevented by the ward (21) in the groove (57).

The safety guide has a "one-shot" system: which system is explained now. Once a trochar has been into the tissue of a patient, it may never be used again. The once used trochar must be returned directly to the safety sheath and discarded. This is defined herein as "one-shot". To affect this "one shot" system, the safety guide has the following design:

See FIG. 10, b. As the trochar is pivoted down with the sheath and the receiver, and locked into the "V" groove on the holder, the receiver locates down onto the one-shot/thumb press housing (54). The receiver housing (11) depresses the "receiver down indicator button" (28). This button is the top portion of a rod which, when it is "down", acts as an upward limiting stop to the first end of the "and/or" beam (30) (See FIG. 6). In FIG. 10b, the button (28) is up. When the receiver (11) is down, as shown in FIG. 10a., it pushes the button (28) down. Note that in FIG. 10, in both views the key (29) is down. FIG. 6a is a partially cutaway side view of the one-shot mechanism. The receiver is down in this figure. For clarity, the trochar is present, but not shown in this figure. Please note that in FIG. 8, a cutaway side view of the safety guide shows a cross section of the one-shot mechanism. In this view, the receiver is down as it is in FIG. 6. However, in this view, the thumb press bar is not depressed. The crickle (31) is "broken"; that is, the upper section is at a significant angle to the lower section.

When the crickle (31) is "broken" it is shorter than when it is straight. In FIG. 6, the thumb press bar (12) is fully depressed. Attached to the thumb press bar is a beam, the thumb press beam (55). This beam is acting upon the crickle (31). The action of pressing on the bar (12) advances the beam (55) of the thumb press bar against the center of the crickle (31). This straightens the crickle and makes it longer. In FIG. 8, the crickle is broken, and because it is shorter it does not push up on the and/or beam (30). In FIG. 6, the crickle is straightened by depressing the thumb press, and therefore becoming longer, it pushes up on the and/or beam. The "and/or" beam has a first end touching the receiver down indicator button (28). The second end of the and/or beam is shown in FIG. 6a, pushing the key (29) upward. That is because the receiver is down, pushing down on the down indicator (28), which affects an upper limit on the first end of the and/or beam. The second end of this beam (30), therefore, pivots upward and pushes up the key (29), as shown in FIG. 6a. The key (29) has a wedge-shaped upper end. This wedge unlocks the trochar from the safety sheath. This action is shown in FIG. 6 and in more detail in FIG. 5. It is described in detail here. Note that the locking vane (22) has a central hole (67) (shown in FIG. 5, a), which hole is a snug fit over the trochar, as shown in FIG. 5b. The locking vane is forced by spring (23) against the inside wall of the first end plate (25a). This wall is at an angle to the central axis of the sheath. When inserted, the trochar assumes this same central axis; (it becomes co-axial to) the sheath. Because of the snug fit, and the spring action against the locking vane, which is supported only at one point on the perimeter of the diameter of the vane, the trochar becomes locked against any force in the reverse axial direction. Pulling on the trochar causes the locking vane to tighten onto the trochar rod. To remove the trochar, it is necessary to support the locking vane on the opposite diameter from where it is supported by the angled inside wall of the first end plate (25a). The action of the key (29) advancing upward [FIG. 6(a)] releases the trochar from the sheath by moving the locking vane (22) against the force of spring (23) to the normal (90 degree) angle (27) [as shown in detail in FIG. 5, (27)] relative to the linear axis of the first end of the trochar. FIG. 6a. shows a detail of this key action. The key has a wedge-shaped end, and the wedge fits between the locking vane and the inside wall of the first end plate [FIG. 5 (25a)]. When the key is pushed upward, the wedge on the end of the key supports the locking vane at a normal angle. So, the trochar can be slid out from the confines of the safety sheath. As described above, the safety sheath is locked into the receiver and stays therein until the trochar is replaced into the safety sheath. When the trochar is replaced into the safety sheath, the two can be removed as an assembly from the receiver, when the trochar is released from the holder.

To affect the priority of the receiver mechanism, shown in FIG. 1 (2) and FIG. 9 (2) with carriage (18), over that of the holder mechanism FIG. 1 (3) and FIG. 9 (3) with carriage (19), an extension control is incorporated into the safety guide. A lock groove (46) is incorporated into the support and alignment beam (4). A pawl (44) is spring-loaded, so as to maintain the pawl in the lock groove (46) and therefore prevent the holder sub-assembly (3) from sliding on the beam. Held to the receiver sub-assembly by fasteners at points (77) is the first end of 1-2 vane (43). At the second end, the 1-2 vane has a semi-circular cam (66). FIG. 9(a) shows the receiver mechanism slid to the left along the beam far enough for the cam (66) to contact the pawl (44) which is shown locked into the groove (46). The inset below (a) is enlarged to show details. FIG. 9(b) shows the receiver mechanism slid yet further to the left, such that the cam (66) has pushed the pawl (44) from the slot (46). At this point, it is possible to slide the holder mechanism (3) to the right, as shown in FIG. 9(c).

Because of the 1-2 extension control, the holder will not slide on the beam until the receiver is fully extended on the beam. This means that in opening the safety guide, the receiver sub-assembly slides completely open before the holder slides at all. That is, when opening the safety guide, the receiver subassembly slides first, and when it is fully extended, the holder slides next, until it is fully extended or the safety guide is open as far as required.

When the trochar sharp point (6) clears the locking vane, the trochar is free from the safety sheath. Refer to FIG. 14. Just before the end of the sharp point is exposed to personnel, the receiver assembly has moved along the beam (4), to the left in this figure. The enlarged end-view, FIG. 6a. (upper right in the figure), shows the feet (33a and b) straddling a slot (34) in the beam (4) and therefore supported by the beam. As the receiver assembly (2) moves beyond a certain limit, at which limit the trochar point is almost exposed, the end of beam (4) passes the boot feet (33) and the boot feet are no longer supported. The feet drop. The feet are connected to the boot (32) and this, in turn, is connected to the lower link of the crickle (31). See FIG. 6b. When the feet are no longer supported by the beam, the boot slides downward, allowing the crickle to straighten and allowing the second end of the and/or beam to descend, therefore allowing the key (29) to return to the "down" position. It will be appreciated that at this combination of conditions, were the trochar to be re-inserted into the safety sheath, it would be locked therein. Also, note that in this combination of conditions, pushing the thumb bar will have no effect upon the key (29) because the crickle is unsupported by the boot, which is unsupported by the beam. Therefore, were the trochar inserted into the target, it could not be withdrawn from the safety sheath, nor could the safety sheath be removed from the receiver. This completes the "one/shot" progression.

To open the safety guide, press the thumb press bar (12) as shown in FIG. 1 and slide the receiver assembly (2) of the safety guide away from the holder assembly (3) on the support beam (4). Slide the safety guide open as far as desired; far enough to receive the tissue flap. See FIG. 15. Insert the tissue flap (75) as shown in FIG. 16. There is room for a large section of tissue. Determine where the tube (7) should be placed in the soft tissue and put the target (5), FIG. 1, at that location. The target center (72), as shown in FIG. 1, is exactly where the sharp point will protrude through as it pierces the tissue. Having established where the drain should be and having placed the target at that spot, pull the handles (10) together, closing the safety guide and safely piercing the tissue with the trochar. When completely closed, as shown in FIG. 19, with the receiver and holder sections of the safety guide pulled together, the trochar has been inserted fully into the safety sheath. The trochar may not be removed from the safety sheath again. This is because the boot (32) is down against the slot (34) of the beam (4) (See FIG. 6). The sharp point and any hazardous materials on and around the point are safely locked into the safety sheath, forever.

To release the trochar from the grip of the holder elements, it is necessary that both sections (holder and receiver) are fully slid together back onto the beam (4) and that the sections are touching each other. With the above conditions satisfied, it is possible to rotate the lever (9) upwards as shown in FIG. 18. Rotating lever (9) causes the torsion rod (38) to rotate. The crank journals (74a and b) move with the rotation of torsion rod (38). See FIG. 8. Therefore, rotating the torsion rod causes the jack (40) to move upward. This push-up acts upon the ram support guide (60) of block (37) (FIG. 7), causing the block to advance against the holder actuator spring (35). The upward advance of the block causes the actuator levers (36) (FIG. 7) to angulate and become shorter, and therefore causes the holding elements (8) to open away from the trochar. See FIG. 7. The trochar, thus released, is pushed out of the "V" groove by the action of the sensor button (58). When the sensor button is fully extended by the sensor spring (63), the locking balls flow into the outer race where they are retained by the holes (71) in the ram wall. In this condition, the balls serve as detents to prevent the support ram (59) from moving down by the force of the holder actuator spring (35), which action would close the holding elements (8). Therefore, the holder elements are now open and remain open until something pushes upon the sensor button (58).

See FIG. 6. As the safety guide is fully closed by sliding the receiver sub-assembly (2) onto the beam (4), the feet (33a and b) enter the groove (34) in the beam. The upper portion of the feet pair is not as wide as the lower portion, and, therefore will fit into the groove (34). Rotating lever (9) and thereby rotating torsion rod (38) also through crank journal (74a) actuates jack (42). But, there is a rotation delay, which causes jack (42) to deploy after jack (40). Therefore, the trochar is released from the holder before jack (42) has been fully actuated. Jack (42) acts upon pushrod (41) in FIG. 8. Pushrod (41) acts upon the boot (32) as shown in FIG. 6. Boot (32) is connected with the lower lever of crickle (31). Pushing up upon the boot pushrod raises the boot, and the feet (33a and b). The upper ends of the feet are pivoted on pins. As the feet pass through the groove (34) in the beam, they are forced together into a closer pattern. When completely past the restriction of the walls of the groove, the feet expand to the larger pattern by the action of two click springs, (not shown, for the sake of clarity). In the expanded, larger pattern, the feet will not pass down through the groove, but instead rest upon the top of the beam, as shown in FIG. 6a. When atop the beam, the feet straddle the groove and hold the boot up to the first position where it supports the crickle. However, since the receiver down indicator button (28) is in the "up" position, no longer held down by the presence of the receiver (11), the and/or beam has no upward limitation on the first end. Therefore, even if the thumb press bar were to be pushed in and the crickle straightened to affect its full length, the and/or beam would not tilt up at the second end. Therefore, the key (29) can not be pushed up without the receiver being in the down position.

With the trochar second end free of the holder, and the first end fastened within the safety sheath (which is itself locked into the receiver), the safety guide may be pivoted about the receiver pivot (15) (FIG. 3). The handles (10) are then at right angles to the trochar. See FIG. 19. In this attitude, the handles provide a very good grip for pulling the trochar with the tube through the tissue flap (75). Pull as much tubing as desired. Then, cut the excess tubing and remove the safety guide and trochar from the sterile field. In the vicinity of the sharp waste container, and as per FIG. 20, exert a slight pressure to further angulate the trochar and the receiver against the ridge vane (16), FIG. 10. The pressure of the ridge vane upon the tail (49) of the pawl (17) will raise the nose (50) of the pawl, extracting it from the notch (51) in the safety sheath, thus releasing the safety sheath with the locked-in trochar. Simply throw the used trochar with the safe sheath into the sharp waste container.

CONCLUSION, RAMIFICATIONS AND SCOPE OF INVENTION

Thus, the reader will see that the safety guide and safe trochar of this invention provide hardware that holds a trochar (or other sharp instrument) as it is being inserted through the skin, from within or from without the patient's body, such that the trochar will be accurately, controllably, and safely guided with good directional stability. Our safe trochar is presented with a protective, inviolable covering: a safety sheath that is on the trochar during shipment, as delivered into the sterile field, and that receives the sharp pointed end of the trochar or other sharp instrument upon exit from the soft tissue. The safety sheath of this invention is designed to work with a number of trochar point designs, including combinations of designs. The target of this hardware allows the surgeon to know exactly where the trochar point will emerge from tissue. Our safety guide provides a "back-up" support for tissue. This support backs up the tissue against the force of the piercing instrument. In this system, the trochar goes directly into the safety sheath as it breaks through tissue; therefore, personnel are inherently safe from the point. Still further, our safety guide provides a handle which is used for pulling the trochar through the tissue, thus saving the surgeon the effort of grabbing the trochar with an additional instrument to enable him to pull the trochar and tube through the soft tissue. Yet further, our safety guide provides a system for ensuring that a trochar is used only one time. And further, the trochar may not be removed from the safety guide without first closing the guide, thereby ensuring that the trochar point is replaced into the sheath and OR personnel are protected from punctures and scratches.

While our above description contains many specficities, these should not be construed as limitations of the scope of the invention, but rather as an exemplification of one preferred embodiment thereof. Many other variations are possible. For example:

In another embodiment of this hardware, the target/receiver is in a hand-held protective disk. The disk is large enough such that it provides protection to an operator's hand. This disk has integral hardware for receiving and retaining the safe trochar within the sheath, as in the receiver in the preferred embodiment. The safe trochar is provided with a sheath. The sheath locks into the receiver in the palm size disk.

Yet another embodiment of this invention is a safety guide on which the target may be rotated out of the line of action of the trochar (or other sharp instrument), therefore allowing the sharp instrument to penetrate tissue straight on, without the target in the path. In this case, upon removal of the sharp instrument from the patient's tissue, the target and safety sheath will rotate back into the line of the sharp instrument and cover the sharp point after use.

A further embodiment of this hardware is a target with a filler that is spring loaded. When the trochar is removed, the plastic filler slides into the opening vacated by the trochar.

The guide of this invention may be provided without a "one-shot mechanism". The guide may be provided with an integral cutter such that the tubing can be cut without having to reach for scissors. The guide can be actuated on a scissors mechanism instead of sliding on a support beam. The guide can be articulated as well as slidably opened.

Different materials may be used in various parts of the hardware of this invention. For example, the trochar can be made of plastic, or of a number of different metals. The guide can be constructed in part or wholly of plastic as well as a number of different metals.

The trochar can be hollow as well as solid. The trochar can be straight as well as curved. The curve of the trochar can be of one of a number of different radii. The diameter of the trochar may be one of a number of different values, and may also be a combination of values. The trochar may have one of a number of different points: faceted, or coned or truncate.

The trochar/sheath locking system can consist of "toggled" fingers; these elements folding to pass through a hole, then expanding beyond it. Alternatively, the locking mechanism can be a groove and a pawl. The locking system can also be a rotational ward.

The reset mechanism can be actuated by a push or pull mechanism instead of, or in addition to, a lever.

Accordingly, the scope of the invention should be determined not by the embodiments illustrated, but by the appended claims and their legal equivalents.

We claim:

1. A safety guide for placing a sharp instrument through the skin of a patient, comprising:
   a first end of a safety guide having a receiver mechanism adapted for lockably accepting a sharp point of the sharp instrument;
   a second end of a safety guide having a holder mechanism adapted for releasably securing the sharp instrument in all directions; and
   a guide beam having a linear elongated body and a substantially uniform cross-section along its length, wherein the receiver mechanism and the holder mechanism are guided in continuous linear alignment along at least a portion of the guide beam such that the sharp point of the sharp instrument follows a substantially straight line from within the receiver mechanism to a position apart from the receiver mechanism and back into the receiver mechanism when the safety guide is actuated, wherein the receiver mechanism includes a receiver having an end face defining an open bore-hole; and wherein the safety guide first end further includes a receiver standard fixed to one end of the guide beam and configured to support the receiver, a receiver pin that intersects the receiver and the receiver standard, and a releasable safety sheath having an elongated cylindrical body defining a diameter substantially the same as the bore-hole, such that the safety sheath is releasably insertable into the open bore-hole.

2. The sharp instrument and safety guide of claim 1, wherein the safety guide first end further includes a sheath-retaining pawl having a portion thereof selectively engagable with a notch in the safety sheath so that the safety sheath is selectively removable from the receiver bore-hole.

3. The sharp instrument and safety guide of claim 2, wherein the receiver standard also has a protruding ridge vane for activating the pawl, wherein the receiver is rotatable about the receiver standard on the receiver pin, whereby rotation of the receiver about the receiver pin causes the ridge vane to engage the sheath-retaining pawl thereby releasing the safety sheath from the receiver bore-hole.

4. The sharp instrument and safety guide of claim 1, wherein the safety sheath includes a target at an end face of the cylindrical body facing the holder mechanism and defines a round hole substantially the same diameter as a shaft of the sharp instrument and configured to receive the instrument point, and further defines a cylindrical interior cavity, wherein the round hole extends through the target to the interior cavity.

5. The sharp instrument and safety guide of claim 1, wherein the safety sheath further includes a positionable locking vane, a compressible sheath spring, and opposing first and second end faces of the interior cavity, wherein the compressible sheath spring and the positionable locking vane lie within the interior cavity and are substantially concentric with a longitudinal axis of the interior cavity, and wherein the locking vane and the compressible sheath spring are interpositioned between the opposing first and second end faces, and the first end face is non-normal to the longitudinal axis of the interior cavity so that when the locking vane is pressed against the non-normal first face an interior edge of the locking vane engages the sharp instrument preventing the removal of the sharp instrument from the safety sheath.

6. The sharp instrument and safety guide of claim 5, wherein the first end of the safety guide further includes a key having a wedge-shaped tip and oriented substantially perpendicular to the longitudinal axis of the interior cavity so that by inserting the key between the locking vane and the first end face of the interior cavity, in opposition to a compression force generated by the compressible sheath spring, the locking vane becomes oriented substantially normal to the longitudinal axis, relieving interference between the locking vane and the received sharp instrument, whereby the sharp instrument can be removed from the safety sheath.

7. A safety guide for placing a sharp instrument through the skin of a patient, comprising:
- a first end of a safety guide having a receiver mechanism adapted for lockably accepting a sharp point of the sharp instrument;
- a second end of a safety guide having a holder mechanism adapted for releasable securing the sharp instrument in all directions; and
- a guide beam having a linear elongated body and a substantially uniform cross-section along its length, wherein the receiver mechanism and the holder mechanism are guided in continuous linear alignment along at least a portion of the guide beam such that the sharp point of the sharp instrument follows a substantially straight line from within the receiver mechanism to a position apart from the receiver mechanism and back into the receiver mechanism when the safety guide is actuated, wherein the safety guide first end further includes a key and a thumb press bar configured to engage the key, wherein actuation of the key aligns a locking vane substantially normal to a longitudinal axis of a received sharp instrument, enabling removal of the received sharp instrument from the receiver.

8. The sharp instrument and safety guide of claim 7, wherein the guide beam further includes a slot and a boot selectively supported by the guide beam and a crickle configured to be reversibly straightened by actuation of the thumb press bar, wherein by straightening the crickle the selectively supported boot is advanced into in the guide beam slot, preventing removal of the sharp instrument from the receiver mechanism when the safety guide is re-closed.

9. A safety guide for placing a sharp instrument through the skin of a patient, comprising:
- a first end of a safety guide having a receiver mechanism adapted for lockably accepting a sharp point of the sharp instrument;
- a second end of a safety guide having a holder mechanism adapted for releasable securing the sharp instrument in all directions; and
- a guide beam having a linear elongated body and a substantially uniform cross-section along its length, wherein the receiver mechanism and the holder mechanism are guided in continuous linear alignment along at least a portion of the guide beam such that the sharp point of the sharp instrument follows a substantially straight line from within the receiver mechanism to a position apart from the receiver mechanism and back into the receiver mechanism when the safety guide is actuated, wherein the holder further includes a groove positioned longitudinal to a second longitudinal axis of the sharp instrument, at least one pair of holder element levers, each lever having a first and second end, wherein the first end of each holder element lever is positioned opposite the first end of its pair and with the groove positioned substantially between the first ends, and a reset lever, wherein at least one element lever of each pair is configured to pivot on an element lever pivot pin, so that by turning the reset lever the first end of at least one element lever moves toward or away from the first end of its pair, thereby holding or releasing a shaft of the sharp instrument.

10. The sharp instrument and safety guide of claim 9, wherein the holder further includes a ram and a ram support guide, wherein the ram support guide is configured to enable the ram to slide longitudinally along an axis common to both the ram and the ram support guide substantially perpendicular to the groove, an actuator block, wherein the ram is fixed to the actuator block, so that the actuator block slides with the ram, an actuator spring, wherein sliding of the actuator block is aided by the actuator spring, and at least one pair of force-multiplying levers, wherein the at least one pair of force-multiplying levers mechanically couple the actuator block to the second ends of the at least one pair of holder element levers, and wherein turning the reset lever pivots at least one holder element lever of each holder element lever pair.

11. A safety guide for placing a sharp instrument through the skin of a patient, comprising:
- a first end of a safety guide having a receiver mechanism adapted for lockably accepting a sharp point of the sharp instrument;
- a second end of a safety guide having a holder mechanism adapted for releasable securing the sharp instrument in all directions; and
- a guide beam having a linear elongated body and a substantially uniform cross-section along its length, wherein the receiver mechanism and the holder mechanism are guided in continuous linear alignment along at least a portion of the guide beam such that the sharp point of the sharp instrument follows a substantially straight line from within the receiver mechanism to a position apart from the receiver mechanism and back into the receiver mechanism when the safety guide is actuated, wherein the first end of the safety guide, the second end of the safety guide, and the guide beam are configured to cooperatively guide the point of the sharp instrument into the receiver, placing the sharp instrument safely through the skin of a patient.

12. The sharp instrument and safety guide of claim 1, wherein a safety sheath of the first end of the safety guide is configured to be permanently fixed to the point of the sharp instrument after one placement of the instrument through a patient's skin.

* * * * *